US006381009B1

(12) United States Patent
McGahan

(10) Patent No.: US 6,381,009 B1
(45) Date of Patent: Apr. 30, 2002

(54) ELEMENTAL CONCENTRATION MEASURING METHODS AND INSTRUMENTS

(75) Inventor: William A. McGahan, San Jose, CA (US)

(73) Assignee: Nanometrics Incorporated, Milpitas, CA (US)

( * ) Notice: Subject to any disclaimer, the term of this patent is extended or adjusted under 35 U.S.C. 154(b) by 0 days.

(21) Appl. No.: 09/343,209

(22) Filed: Jun. 29, 1999

(51) Int. Cl.$^7$ .................. G01N 21/00; G01N 21/21; G01J 4/00; G01B 11/06
(52) U.S. Cl. ................... 356/73; 356/369; 356/630
(58) Field of Search ................. 356/445, 446, 356/369, 630, 73

(56) References Cited

U.S. PATENT DOCUMENTS

| | | | |
|---|---|---|---|
| 5,136,514 A | 8/1992 | Laumann | 364/464.04 |
| 5,285,167 A | 2/1994 | Carangelo | 330/10 |
| 5,349,438 A | 9/1994 | Solomon | 356/346 |
| RE34,783 E | 11/1994 | Coates | 250/372 |
| 5,373,359 A | 12/1994 | Woollam et al. | 356/328 |
| 5,403,433 A | 4/1995 | Morrison et al. | 156/626 |
| 5,432,336 A | 7/1995 | Carangelo et al. | 250/214 L |
| 5,473,429 A | 12/1995 | Carangelo et al. | 356/345 |
| 5,486,917 A | 1/1996 | Carangelo et al. | 356/346 |
| 5,604,581 A | 2/1997 | Liu et al. | 356/73 |
| 5,900,633 A | 5/1999 | Solomon et al. | 250/339.08 |

OTHER PUBLICATIONS

Cox, J.N., et al., "FTIR spectrophotometry for thin film monitors: computer and equipment integration for enhanced capabilities," *Advanced Techniques for Integrated Circuit Processing*, SPIE Proceedings.

McGahan, W.A., et al., "Optical Characterization of TiN Thin Films," Advanced Semiconductor Manufacturing Conference and Workshop (ASMC), 1996 IEEE/SEMI, pp. 359–363.

McGahan, W.A., et al., "Combined Spectroscopic Ellipsometry and Reflectometry for Advanced Semiconductor Fabrication Metrology," *Optical Characterization Techniques for High–Performance*.

Press, W.H., et al., *Numerical Recipes in C: The Art of Scientific Computing*, Cambridge University Press, 2nd ed., 1992.

Tompkins, H.G. and McGahan, W.A., *Spectroscopic Ellipsometry and Reflectometry: A User's Guide*, John Wiley & Sons, Inc., 1999.

Metrology that Measures Up, *Solid State Technology*, Apr. 1997, p. 83.

Metrology that Measures Up!, Metrology Systems, Moore Technologies Web Site (http://www.mooretech.com/metrology.htm), 1996, 2 pages.

MIR 8000™ Modular IR Fourier Spectrometer, Oriel Instruments, 250 Long Beach Blvd., Stratford, CT 06497, product information, pp. 1–10.

The Illuminator, MIDAC Corporation, 17911 Fitch Avenue, Irvine, CA 92714, product information, 2 pages.

*Primary Examiner*—F. L. Evans
*Assistant Examiner*—Zandra V. Smith
(74) *Attorney, Agent, or Firm*—Skjerven Morrill MacPherson LLP; Michael J. Halbert

(57) ABSTRACT

An instrument and methods are used to determine film layer thicknesses, optical constant spectra, and elemental concentrations of a sample substrate overlaid with a single or multiple films. The instrument measures the sample substrate's absolute reflectance and ellipsometric parameters over a first set of wavelengths to determine film layer thicknesses and optical constants of the film layers over the first set of wavelengths. The instrument also measures the sample substrate's absolute reflectance or transmittance over a second set of wavelengths. Based on these measurements and analysis, the instrument determines at least one element's concentration in at least one film layer of the sample substrate.

21 Claims, 21 Drawing Sheets

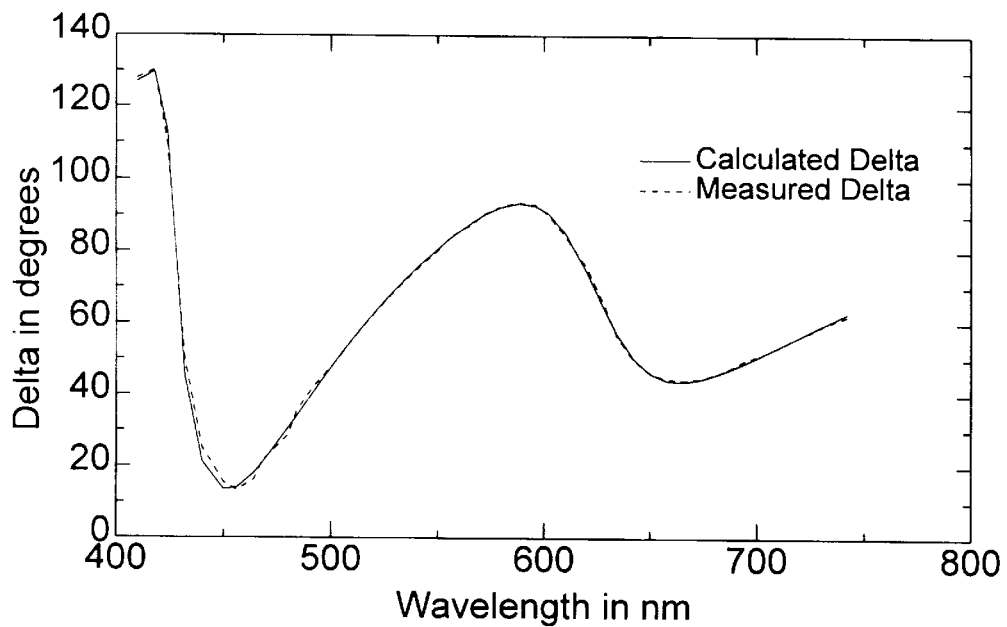
FIG. 8
| Titanium Nitride | 248 Angstroms |
| Silicon Dioxide | 4997 Angstroms |
| Silicon | Substrate |
FIG. 9
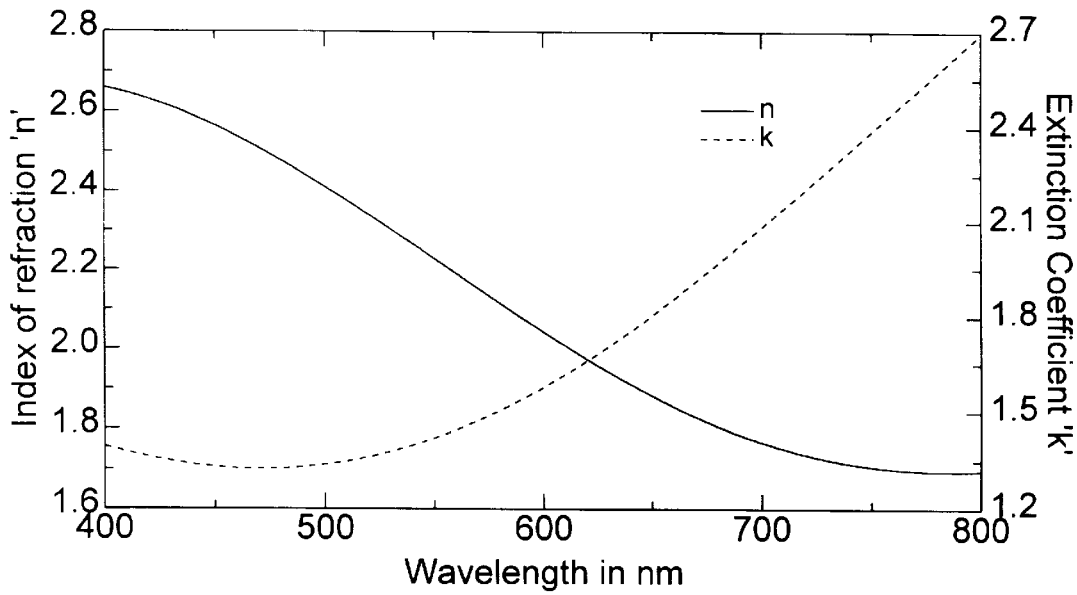
FIG. 10

| Sample # | Thickness (Angstroms) | Flourine Concentration (%F) |
|---|---|---|
| 1 | 3354.2 | 0 |
| 2 | 3536.1 | 0.6683 |
| 3 | 3635.7 | 1.17618 |
| 4 | 3674.2 | 1.29875 |
| 5 | 5937.8 | 0 |
| 6 | 6189.1 | 0.81586 |
| 7 | 6266.0 | 1.35012 |
| 8 | 6277.2 | 1.68495 |
| 9 | 9577.1 | 0 |
| 10 | 9812.5 | 0.8620 |
| 11 | 9844.3 | 1.44264 |
| 12 | 9923.9 | 1.62755 |
| 13 | 10958.0 | 0 |
| 14 | 11164.1 | 0.82734 |
| 15 | 11288.1 | 1.42917 |
| 16 | 11359.7 | 1.70195 |

| Sample # | Thickness (Angstroms) | Integrated Area (Arbitrary unit) | %F |
|---|---|---|---|
| 1 | 3354.2 | 1.48643 | 0 |
| 2 | 3536.1 | 2.72429 | 0.6683 |
| 3 | 3635.7 | 3.45836 | 1.17618 |
| 4 | 3674.2 | 3.773974 | 1.29875 |
| 5 | 5937.8 | 3.611216 | 0 |
| 6 | 6189.1 | 7.50941 | 0.81586 |
| 7 | 6266.0 | 8.497113 | 1.35012 |
| 8 | 6277.2 | 9.26998 | 1.68495 |
| 9 | 9577.1 | 6.78519 | 0 |
| 10 | 9812.5 | 11.03767 | 0.8620 |
| 11 | 9844.3 | 13.15412 | 1.44264 |
| 12 | 9923.9 | 14.20947 | 1.62755 |
| 13 | 10958.0 | 7.03457 | 0 |
| 14 | 11164.1 | 10.82008 | 0.82734 |
| 15 | 11288.1 | 12.72552 | 1.42917 |
| 16 | 11359.7 | 13.68364 | 1.70195 |

ELEMENTAL CONCENTRATION MEASURING METHODS AND INSTRUMENTS

FIELD OF THE INVENTION

The present invention relates to methods and instruments that determine thin film properties from optical measurements.

BACKGROUND

Thin solid films are of tremendous industrial importance in a variety of fields, including semiconductor device manufacturing, flat panel display manufacturing, and magnetic head manufacturing. These films commonly consist of mixtures of elements where the concentrations are varied to control the properties of the films (e.g., electrical, mechanical, tribological). Other important parameters used to control the properties of the films include the thickness and optical constants (index of refraction n and coefficient of extinction k) of the films. As a result, when thin films with multiple elemental constituents are used in production applications, it is often crucial to monitor these parameters to achieve the desired properties.

Commercially available spectral reflectometers and ellipsometers are capable of determining thicknesses and optical constant spectra of thin films by measuring reflectance and ellipsometric parameters psi and delta in the spectral ranges of deep ultra-violet (DUV), e.g., approximately 190 to 400 nm (nanometer), visible (VIS), e.g., approximately 300 to 800 nm, and near infrared (NIR), e.g., approximately 800 to 2500 nm. However, spectral reflectometers and ellipsometers in many cases cannot accurately measure elemental concentration. On the other hand, commercially available Fourier Transform Infrared (FTIR) spectrometers are capable of determining elemental concentration of thin films by measuring reflectance or transmittance in the infrared (IR) spectral range, e.g., approximately 2500 to 25,000 nm. Unfortunately, FTIR spectrometers necessitate the prior knowledge of the film layer thicknesses to accurately determine elemental concentration. Accordingly, a user must first use spectral reflectometers and ellipsometers to determine film layer thicknesses and optical constant spectra, and then use FTIR spectrometers to determine elemental concentration.

The use of multiple instruments in many industries, e.g., semiconductor manufacturing, is undesirable because of the high fabrication and maintenance costs of clean rooms. Further, the use of multiple instruments creates time-consuming transfer of samples from one instrument to another and reduces the accuracy of the instruments because it is difficult for multiple instruments to measure from the exact same area on the samples. Thus, there is a need for an integrated optical measuring instrument and methods that determine thickness, optical constant spectra, and elemental concentration of thin films while minimizing space, increasing throughput, and improving accuracy.

SUMMARY

An instrument and methods are used to determine film layer thicknesses, optical constant spectra of film layers, and elemental concentrations of a sample substrate overlaid with single or multiple films, in-situ or ex-situ, rapidly, non-destructively, without contact, and on a real-time basis. The instrument measures the sample substrate's absolute reflectance and ellipsometric parameters psi and delta over a first set of wavelengths, e.g., DUV, VIS, and NIR spectral ranges, to determine film layer thicknesses and optical constants of the film layers over the first set of wavelengths. In one embodiment, absolute reflectance is measured in accordance with the method described in U.S. Pat. No. Re. 34,783, entitled "Method for Determining Absolute Reflectance of a Material in the Ultraviolet Range," issued to Vincent J. Coates, which is hereby incorporated by reference in its entirety. The instrument also measures the sample substrate's absolute reflectance or transmittance over a second set of wavelengths, e.g., IR spectral range. Based on these measurements and analysis, the instrument determines one element's concentration in one or more film layers of the sample substrate.

In one embodiment, the instrument determines one element's concentration in a film layer of a film layer structure on a sample substrate by correlating the element's concentration to the film layer's optical constants in the spectral region of an absorption band of that element. The instrument determines the optical constants using the determined film layer thicknesses to fit an optical model to the measured absolute reflectance or transmittance.

In another embodiment, the instrument determines one element's concentration in a film layer of the film layer structure on the sample substrate by relating the element's concentration to the film layer's thickness and an absorption-related feature of the element from the measured absolute reflectance or transmittance. The instrument determines this relationship by analyzing calibration films with known film layer thicknesses and concentrations of the element.

In yet another embodiment, the instrument determines one element's concentration in a film layer of the film layer structure on the sample substrate using a trained artificial neural network (ANN) computer program. The embodiment includes an ANN computer program that is trained with optical constants over the first set of wavelengths, absolute reflectance or transmittance over the second set of wavelengths, film layer thicknesses, and elemental concentrations from calibration samples. Thereafter, the instrument determines the element's concentration in the film layer from the sample substrate's determined film layer thicknesses, determined optical constants over the first set of wavelengths, and measured absolute reflectance or transmittance over the second set of wavelengths.

BRIEF DESCRIPTION OF THE DRAWINGS

The present invention may be better understood, and its numerous objects, features, and advantages made apparent to those skilled in the art by referencing the accompanying drawings.

FIG. 8 is a graph of the measured ellipsometric parameter delta and the calculated (theoretical) ellipsometric parameter delta of the sample silicon substrate overlaid with a silicon dioxide film layer and a titanium nitride film layer.

FIG. 9 is a table of the determined film layer thicknesses of the sample silicon substrate overlaid with a silicon dioxide film layer and a titanium nitride film layer.

FIG. 10 is a graph of the determined optical constants of the titanium nitride film layer of the sample silicon substrate overlaid with a silicon dioxide film layer and a titanium nitride film layer.

FIG. 18b is a prediction flow chart of the method of FIG. 18a.

FIG. 29b is a prediction flow chart of the method FIG. 29a.

The use of the same reference symbols in different drawings indicates similar or identical items.

DETAILED DESCRIPTION

Figure 1:
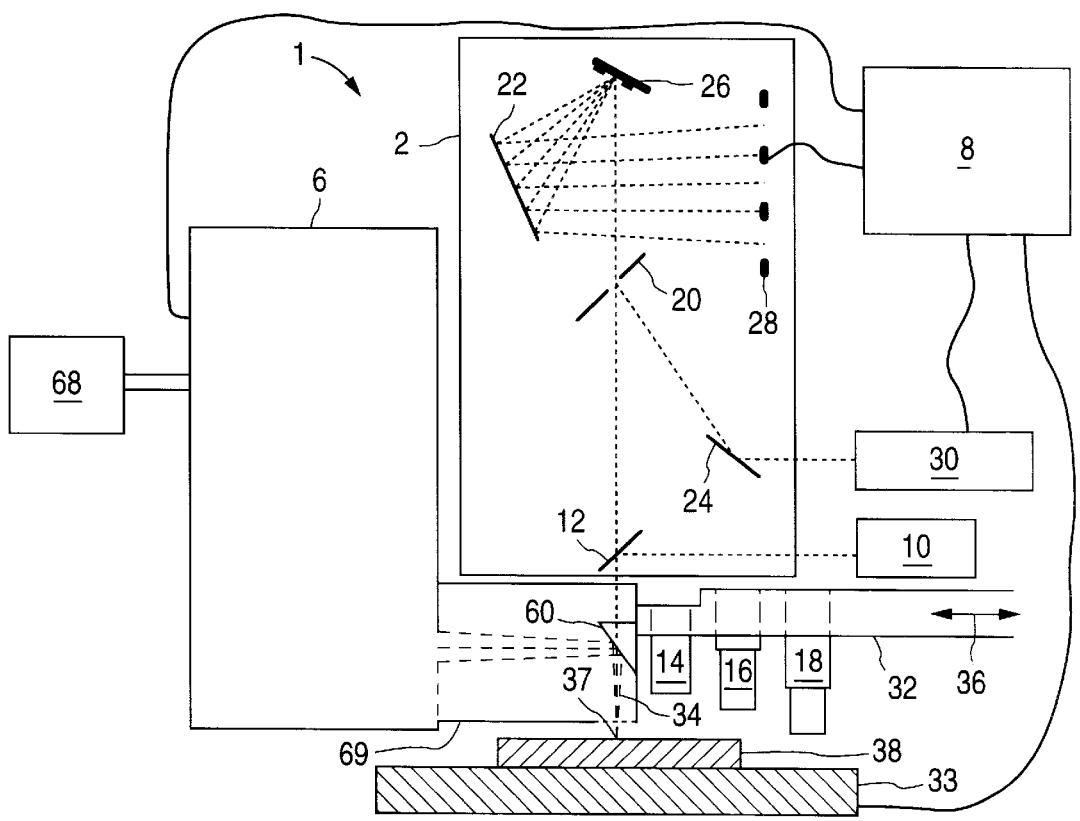
FIG. 1 is a diagram illustrating an integrated optical measuring instrument used in accordance with one embodiment of the present invention.
Figure 2:
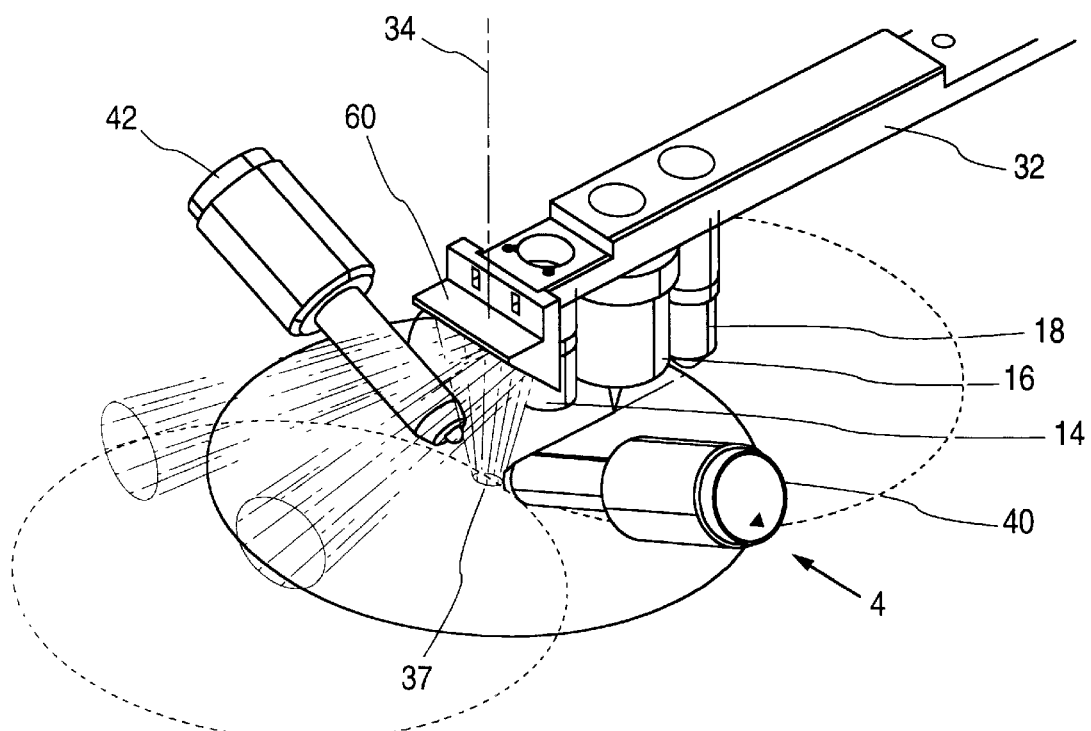
FIG. 2 is a diagram of the integrated optical measuring instrument of FIG. 1 from a different viewing angle.

FIGS. 1 and 2 illustrate an integrated optical measuring instrument 1 used in accordance with one embodiment of the present invention. Integrated optical measuring instrument 1 includes a DUV-NIR reflectometer 2, a VIS ellipsometer 4 (shown in FIG. 2 as including components spectroscopic ellipsometer lamp 40 and ellipsometer detector 42), a FTIR spectrometer 6, and a microprocessor 8.

As shown in FIG. 1, DUV-NIR reflectometer 2 includes a light source 10, a beam splitter 12, objective lens 14, 16, 18, mirrors 20, 22 and 24, a diffraction grating 26, a detection array 28, an imaging device 30, a linear turret 32, and a stage 33. In operation, linear turret 32 aligns a selected objective lens, e.g., objective lens 18, with a vertical axis 34 by a linear movement 36. Light source produces light at selected wavelengths, e.g., 190–800 nm, towards beam splitter 12, which redirects a fraction of the light to objective lens 18. Objective lens 18 focuses the light onto an area 37 on a sample 38 that rests on stage 33, where some of the light is reflected back through objective lens 18, beam splitter 12, and onto mirror 20. A hole in mirror 20 passes some of the light to diffraction grating 26, which reflects the light spectrally to detection array 28 by way of mirror 22. Mirror 20 reflects the remaining light to imaging device 30 by way of mirror 24.

As shown in FIG. 2, VIS ellipsometer 4 includes a spectroscopic ellipsometer lamp 40 and ellipsometer detector 42. Spectroscopic ellipsometer lamp 40 includes a conventional polarizer (not shown), and ellipsometer detector 42 includes a conventional rotating analyzer (not shown). In operation, spectroscopic ellipsometer lamp 40 produces and directs a polarized light at selected wavelengths, e.g., 400–750 nm, toward sample 38 (not shown in FIG. 2). Spectroscopic ellipsometer lamp 40 and ellipsometer detector 42 are positioned such that the light reflects off area 37 on sample 38 and is received by ellipsometer detector 42. In the embodiment shown, VIS ellipsometer 4 is an instrument described in U.S. Pat. No. 5,373,359, entitled "Ellipsometer," issued to Woollam et al., which is hereby incorporated by reference in its entirety.

Figure 3:
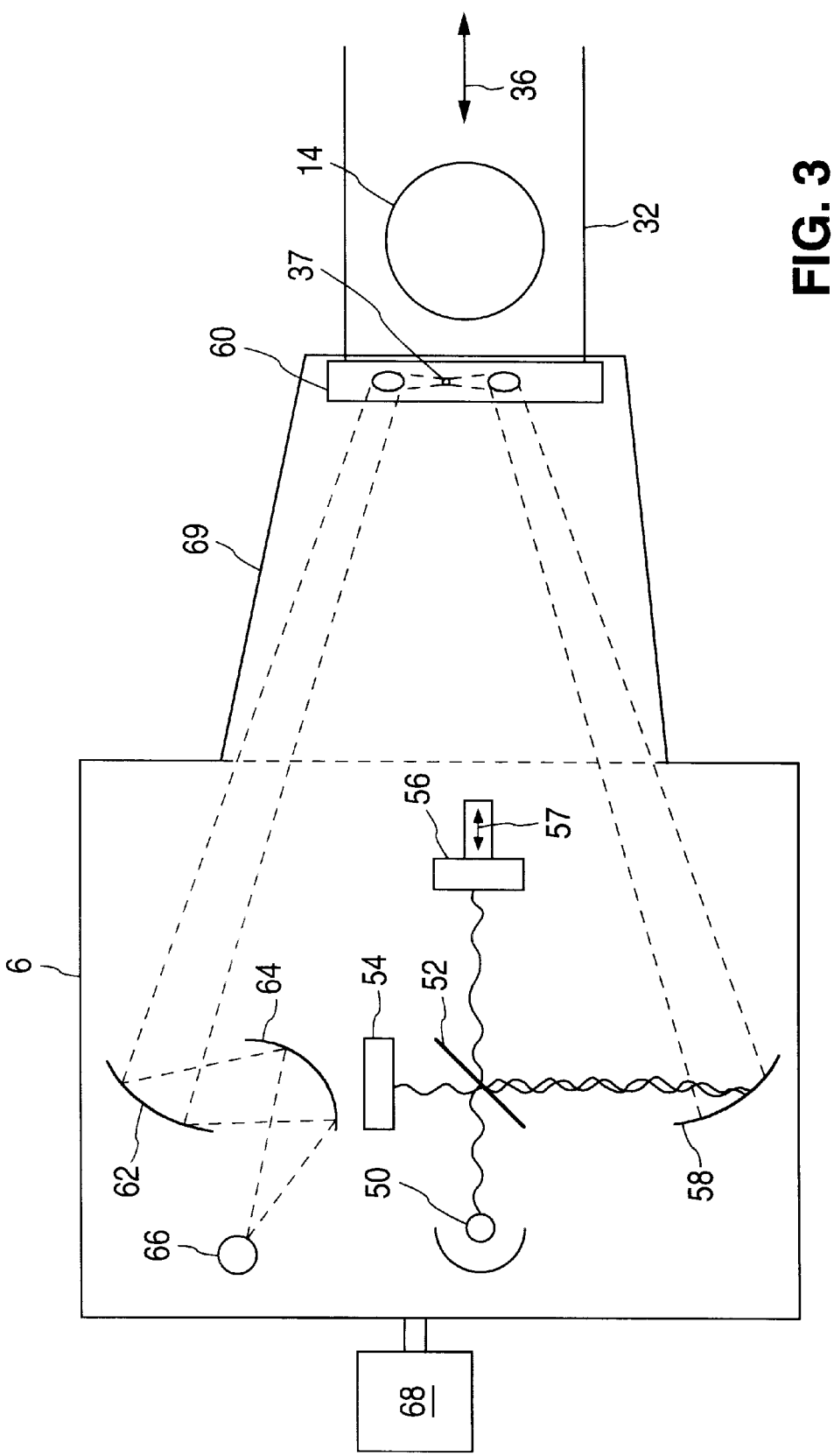
FIG. 3 is a diagram of a FTIR spectrometer that is a part of the integrated optical measuring instrument shown in FIGS. 1 and 2.

As shown in FIG. 3, FTIR spectrometer 6 includes a light source 50, a beam splitter 52, mirrors 54, 56, 58, 60, 62, and 64, a detector 66, a purging gas supply 68, a purging shroud 69, and linear turret 32. In operation, linear turret 32 aligns mirror 60 so that light reflected off mirror 60 is focused on area 37 on sample 38 along vertical axis 34 (not shown in FIG. 3). Light source 50 produces and directs light at selected wavelengths, e.g., 2500 to 25,000 nm, towards beam splitter 52, which redirects a fraction of the light to stationary mirror 54 and moving mirror 56, which moves back and forth as indicated by an arrow 57. As moving mirror 56 moves back and forth, light reflected off moving mirror 56 and stationary mirror 54 are combined constructively, destructively, or somewhere in between. This combination generates a light of multiple wavelengths and phases that change with time from the movement of moving mirror 56. Focusing mirror 58 reflects the combined light to mirror 60, which redirects the light to sample 38 (not shown in FIG. 3). Sample 38 reflects some of the light back to mirror 60. Mirror 60 redirects the light to detector 66 by way of focusing mirrors 62 and 64. During operation, purging gas supply 68 supplies a purging gas to purging shroud 69 to remove water vapor and carbon dioxide in the optical path, thereby preventing instrument inaccuracies due to the presence of these gases in the optical path.

Integrated optical measuring instrument 1 may be for example the instrument described in U.S. patent application Ser. No. 09/113,610 entitled "Integrated Optical Measurement Instruments", filed on Jul. 10, 1998 by Duane C. Holmes, which is hereby incorporated by reference in its entirety.

Note that DUV-NIR reflectometer 2, VIS ellipsometer 4, and FTIR spectrometer 6 can measure from single or multiple angles on a small or large area. Further, DUV-NIR reflectometer 2, VIS ellipsometer 4, and FTIR spectrometer 6 can measure from single or multiple areas on sample substrate 38 by linear movement 36 of linear turret 32. Finally, while the present disclosure discusses the use of DUV-NIR reflectometer 2, VIS ellipsometer 4, and FTIR spectrometer 6, it should be understood that the present invention may use any spectral analysis instruments. For example, integrated optical measuring instrument 1 may include any combination of spectral analysis instruments that measure relative reflectance, absolute reflectance, transmittance, or ellipsometric parameters in the DUV, VIS, NIR, or IR spectral range from single or multiple angles on a large or focused area at one or multiple areas on a sample substrate.

Figure 4:
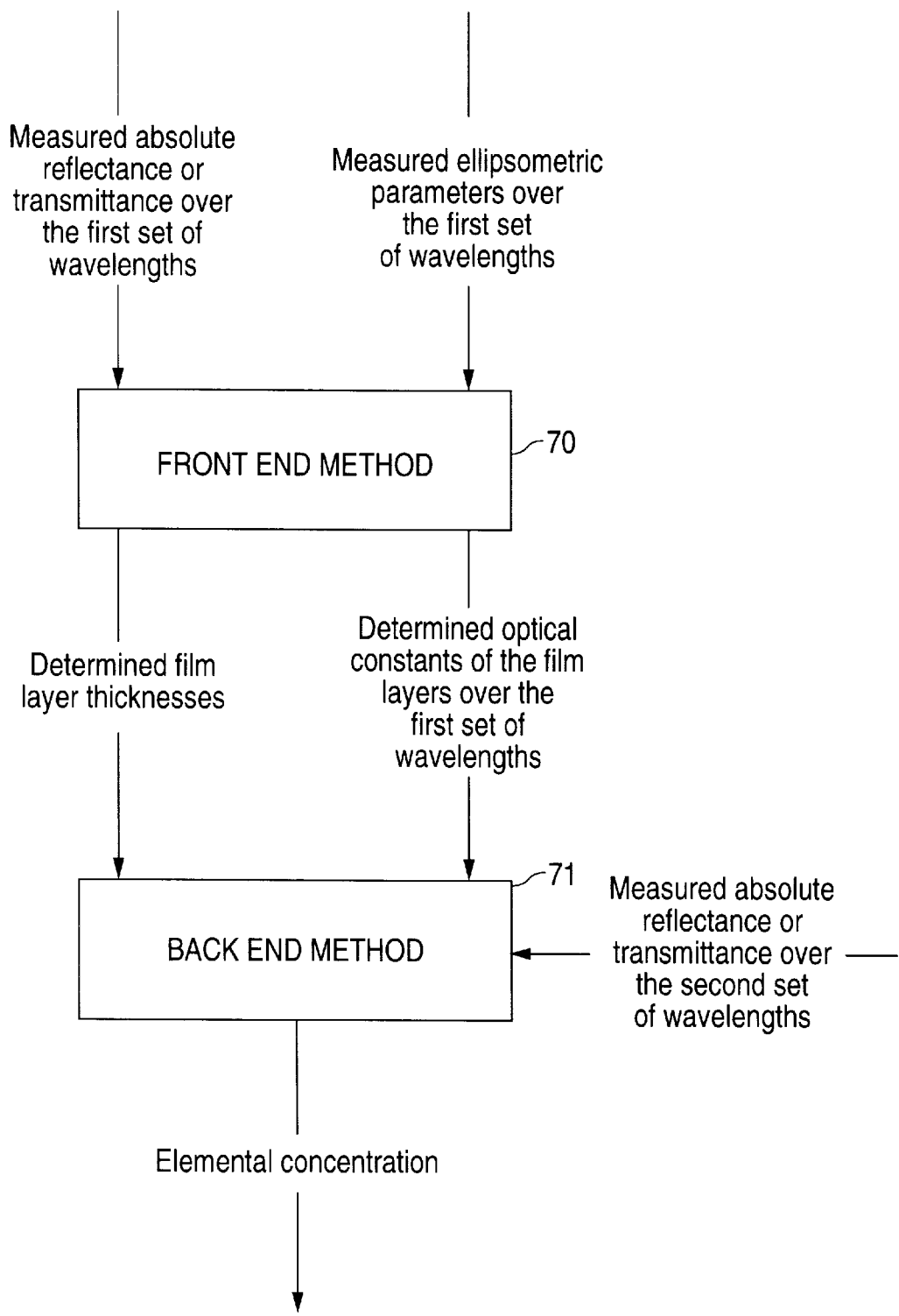
FIG. 4 is a diagram of a front end method and a back end method used in conjunction to determine film layer thicknesses, optical constants of the film layers, and at least one element's concentration in at least one film layer of a substrate overlaid with single or multiple film layers.

FIG. 4 illustrates one embodiment of the present invention where a front end method 70 and a back end method 71 work in conjunction to determine at least one element's concentration from at least one film layer in a film layer structure on a sample substrate. In front end method 70, thicknesses and optical constant spectra of the film layers over a first set of wavelengths, e.g., VIS spectral range, are determined from measured absolute reflectance and ellipsometric parameters over the first set of wavelengths. In back end method 71, elemental concentration is determined from (1) measured absolute reflectance or transmittance over a second set of wavelengths, e.g., IR spectral range, and (2) at least one of (a) the determined film layer thicknesses from front end 70 and (b) the determined optical constant spectra from front end method 70.

Figure 5:
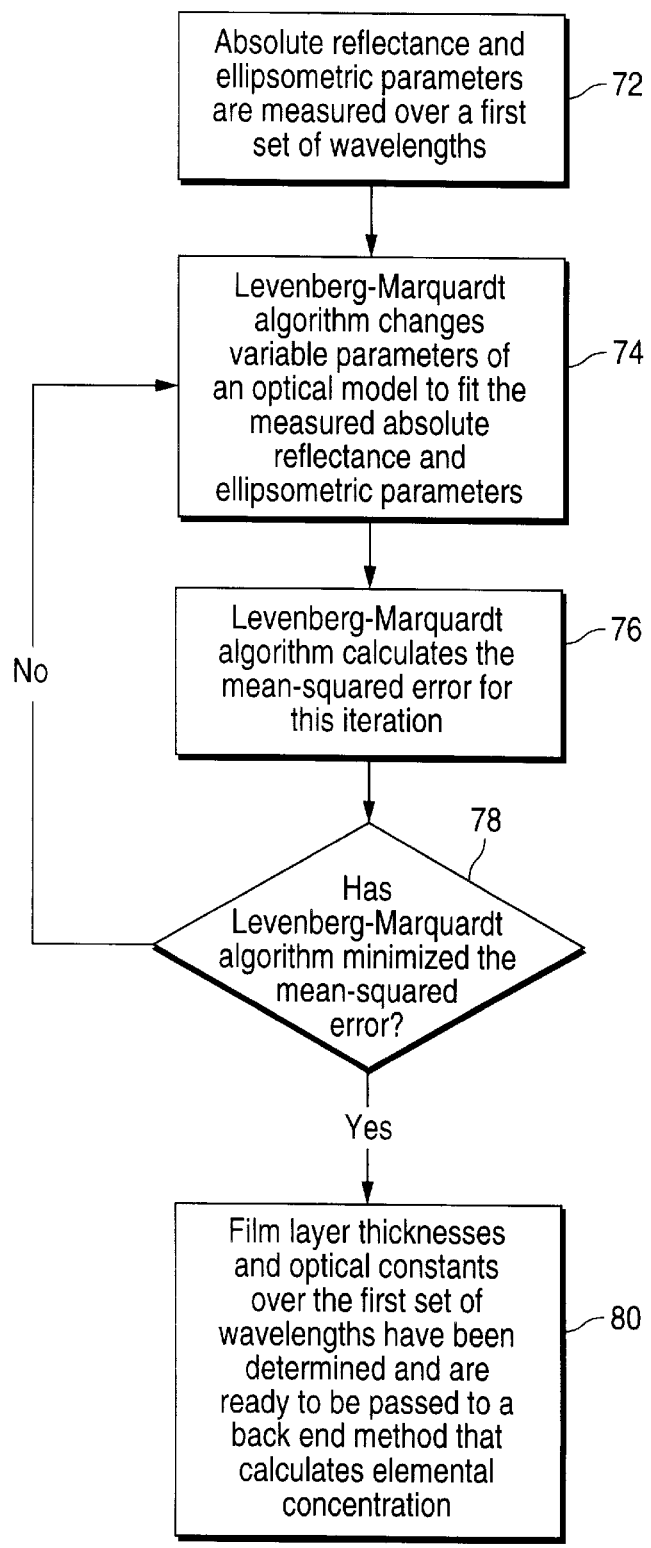
FIG. 5 is a flow chart of a method used to determine film thicknesses and optical constant spectra over multiple wavelengths in thin films.

FIG. 5 illustrates one embodiment of front end method 70 by which integrated optical measuring instrument 1 determines film layer thicknesses and optical constant spectra of film layers over a first set of wavelengths of a sample substrate 38 overlaid with single or multiple thin films. In step 72, DUV-NIR reflectometer 2 and VIS ellipsometer 4 measure absolute reflectance and ellipsometric parameters, respectively, of sample substrate 38 from area 37 over the first set of wavelengths. In steps 74, 76, and 78, microprocessor 8 applies a Levenberg-Marquardt non-linear multivariate regression algorithm to fit an optical model of sample substrate 38 to the measured absolute reflectance and ellipsometric parameters. The Levenberg-Marquardt algorithm is a curve fitting method well understood by those of ordinary skill in the art and is further described in "Numerical Recipes in C" by W. H. Press, S. A. Teukolsky, W. T. Vetterling, and B. P. Fannery, published by Cambridge University Press (1992), which is hereby incorporated by reference in its entirety. Optical models are mathematical formulas that describe optical characteristics of multi-layered structures. Optical models are well understood by those of ordinary skill in the art and are further described in "Spectroscopic Ellipsometry and Reflectometry: A User's Guide" by Harland G. Tompkins and William A. McGahan, published by John Wiley and Sons (1999), which is hereby incorporated by reference in its entirety. An example of commercially available computer programs that use the Levenberg-Marquardt algorithm to fit optical models to measured data is "WVASE32™" by J.A. Woollam Co., located at 645 M Street, Suite 102, Lincoln, Nebr. 68508.

Briefly, the Levenberg-Marquardt algorithm works as follows. In step 74, the Levenberg-Marquardt algorithm selects values for variable parameters in the optical model, e.g., film layer thicknesses and optical constants of the film layers, to calculate theoretical absolute reflectance and ellipsometric parameter values. In step 76, the Levenberg-Marquardt algorithm compares the theoretical absolute reflectance and ellipsometric parameters to the measured absolute reflectance and ellipsometric parameters to determine a mean-squared error defined as:

$$MSE(\overline{x}) = \frac{1}{N-M} \sum_{i=1}^{N} \left( \frac{y_i - y(\overline{x}_i)}{\sigma_i} \right)^2, \qquad \text{Equ. 1}$$

where N is the total number of data points (absolute reflectance and ellipsometric parameters), M is the total number of variable parameters, $y_i$ is the $i^{th}$ data point (absolute reflectance, ellipsometric psi, or ellipsometric delta), $y(\overline{x}_i)$ is the $i^{th}$ calculated data point, $\overline{x}^i$ represents the variable parameters in the optical model, and $\sigma^i$ is the standard deviation of the $i^{th}$ data point. In step 78, the Levenberg-Marquardt algorithm determines if it has minimized the mean-squared error, i.e., if it has reached a best fit. The Levenberg-Marquardt algorithm has minimized the mean-squared error when the slope of the mean-squared error curve reaches zero. If so, the values of the variable parameters, e.g., film layer thicknesses and optical constants of the film layers, are deemed the actual physical values of those parameters. If the Levenberg-Marquardt algorithm has not minimized the mean-squared error, steps 74, 76, and 78 are repeated with another set of values for the variable parameters. In summary, the Levenberg-Marquardt algorithm systematically changes values for film layer thicknesses and optical constants of the film layers to determine a set of values that yields theoretical absolute reflectance and ellipsometric parameters from the optical model that best match the measured absolute reflectance and ellipsometric parameters.

Note that the starting values for the variable parameters in the first iteration of the Levenberg-Marquardt algorithm, i.e., seed values, are provided by the user and are generally the values that manufacturers of the thin films are trying to achieve. Using these seed values, the Levenberg-Marquardt algorithm may achieve either a local or a global minimum of the mean-squared error. To ensure that a global minimum of the mean-squared error is reached, the user may apply the Levenberg-Marquardt algorithm with different seed values to see if the same values for the variable parameters can be achieved. A global minimum of the mean-squared error is probably achieved if different sets of seed values produce the same values for the variable parameters.

Also note that in a substrate overlaid with multiple thin films, the user may fix the optical constants of selected film layers to values listed in available literature well known to those in the art while the optical constants of the other film layers are varied by the Levenberg-Marquardt algorithm.

Further note that the contribution of any given data point to the mean-squared error function will increase if the standard deviation of the measurement decreases. For the ellipsometric data, the standard deviation of each data point can be calculated from the fluctuations of psi and delta observed during the averaging over cycles of the rotating analyzer used in ellipsometer detector 42. Such a calculation is not possible for the standard deviation of the reflectance data and, thus, a reasonable estimate of the standard deviation of the reflectance data must be made. The smaller the value chosen for the reflectance standard deviations, the more strongly the model will be forced to fit the experimental reflectance data at the expense of the ellipsometric data.

Finally, note that where there may be a large number of variable parameters in an optical model, such as in an optical model for a multi-layered structure, and few spectral measurements at overlapping wavelengths, the Levenberg-Marquardt algorithm may produce a solution for the variable parameters that is not unique. In many cases, two or more variable parameters may be strongly correlated such that more than one solution for the variable parameters yield approximately the same match between the theoretical and measured data. Also, it is possible that the theoretical data may not be sensitive to one or more of the variable parameters, such that large changes in that parameter have little or no effect on the calculated data. To detect the occurrence of these problems, the simplest and most effective test is to repeat the measurement and analysis many times on the same sample location and look at the repeatability of the best-fit values of the variable model parameters. If the results of the analysis are not very repeatable, experimentation is required to eliminate the variable parameters for which the data are not sensitive, or identify and eliminate the variable parameters in the model which are correlated.

To help prevent multiple solutions for the variable parameters, parametric dispersion models are used to represent variable parameters of optical constants of the film layers in the optical models. Parametric dispersion models help to produce unique solutions by providing a connection between the ellipsometric and reflectance data and enforcing a physically reasonable dispersion of the optical constants. Parametric dispersion models for numerous materials are well understood by those of ordinary skill in the art and are further described in "Spectroscopic Ellipsometry and Reflectometry: A User's Guide" by Harland G. Tompkins and William A. McGahan, published by John Wiley and Sons (1999), which was previously incorporated by reference. As an example, the Lorentz oscillator dispersion model may be used to describe the optical constants and appears as follows:

$$\tilde{\varepsilon}(E) = [\tilde{n}(E)]^2 = [n + ik]^2 = \varepsilon(\infty) + \sum_{i=1}^{N} \frac{A_i}{E_i^2 - E^2 - iB_iE}, \quad \text{Equ. 2}$$

where E is the photon energy in eV, $\varepsilon E$) is the complex dielectric function expressed as a function of the photon energy E, $\tilde{n}(E)=n+ik$ is the complex index of refraction as a function of photon energy, $\varepsilon(\infty)$ is the (real) value of the dielectric function for infinite energy, N is the number of oscillators, and $A_i$, $B_i$, and $E_i$ are the amplitude, broadening, and center energy of the $i^{th}$ oscillator, respectively.

While the present disclosure discusses the use of both DUV-NIR reflectometer 2 and DUV-NIR ellipsometer 4 in one embodiment of front end method 70, it should be understood that the present invention can use either tool alone to determine film layer thicknesses and optical constants. However, an embodiment of the present invention that uses either tool alone must investigate the uniqueness of the particular solution of the variable parameters determined by the Levenberg-Marquardt algorithm because there are many variable parameters and only one spectral measurement at each wavelength. To help produce a unique solution to the variable parameters, the number of variable parameters can be reduced by assuming certain variable parameters to be zero over certain spectral ranges. For example, the extinction coefficient k of the optical constants for certain materials may be assumed to zero over the VIS spectral range.

Figure 6:
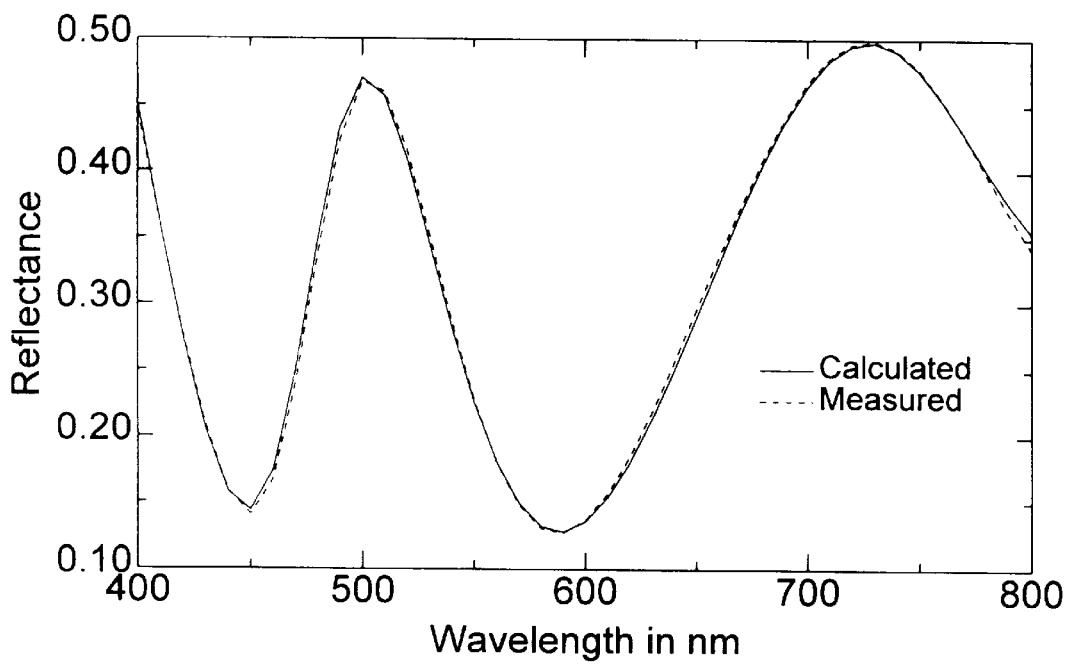
FIG. 6 is a graph of the measured absolute reflectance and the calculated (theoretical) absolute reflectance of a sample silicon substrate overlaid with a silicon dioxide film layer and a titanium nitride film layer.
Figure 7:
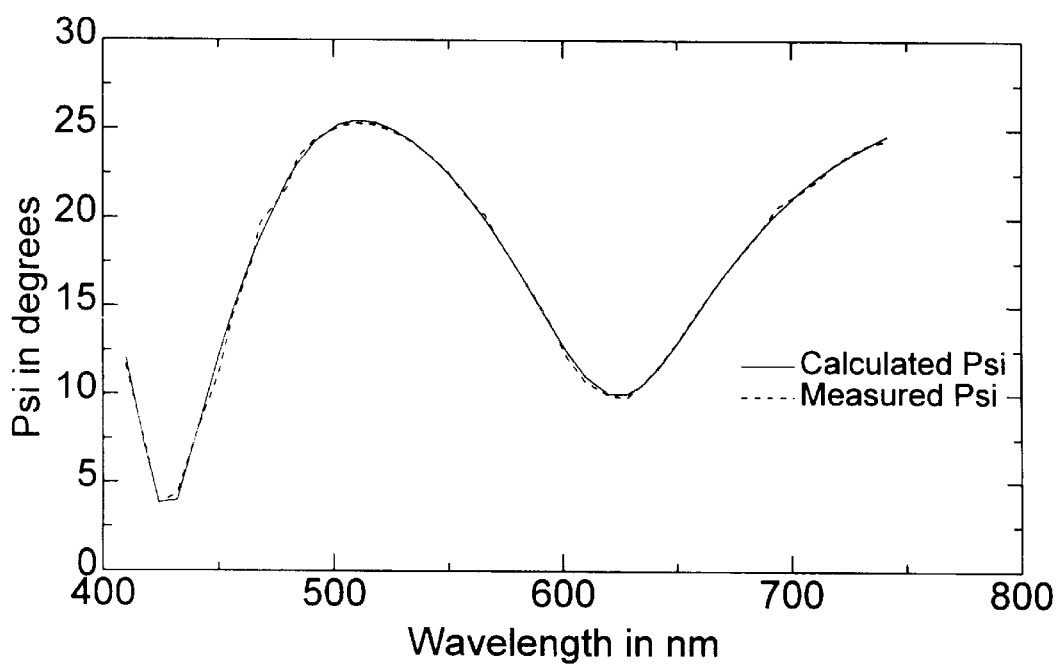
FIG. 7 is a graph of the measured ellipsometric parameter psi and the calculated (theoretical) ellipsometric parameter psi of the sample silicon substrate overlaid with a silicon dioxide film layer and a titanium nitride film layer.

Front end method 70 described above and in FIG. 5 is demonstrated by the following example, where the film layer thicknesses and optical constant spectra are determined for a sample silicon (Si) substrate overlaid first with one film layer of silicon dioxide ($SiO_2$) and then one film layer of titanium nitride (TiN). DUV-NIR reflectometer 2 and VIS ellipsometer 4 first measure the absolute reflectance and ellipsometric parameters, respectively, of the sample silicon substrate. The measured absolute reflectance and ellipsometric psi and delta are shown as solid lines in FIGS. 6, 7, and 8, respectively. Microprocessor 8 then uses the Levenberg-Marquardt algorithm to determine values of variable parameters in the optical model, i.e., film layer thicknesses and optical constants of the TiN film layer, that produce theoretical absolute reflectance and ellipsometric parameters from the optical model that best match the measured absolute reflectance and ellipsometric parameters. In this example, the optical constants of the Si substrate and the $SiO_2$ film layers are set to values stated in available literature. The best fit theoretical absolute reflectance and ellipsometric parameters psi and delta produced by the Levenberg-Marquardt algorithm are shown as dashed lines in FIGS. 6, 7, and 8, respectively. The film layer thicknesses and optical constants of the TiN film layer that produced the best fit are shown in FIGS. 9 and 10, respectively.

Once front end method 70 determines the film layer thicknesses and optical constant spectra of the film layers over the first set of wavelengths, one of several embodiments of back end method 71 may be used to determine elemental concentration.

Figure 11:
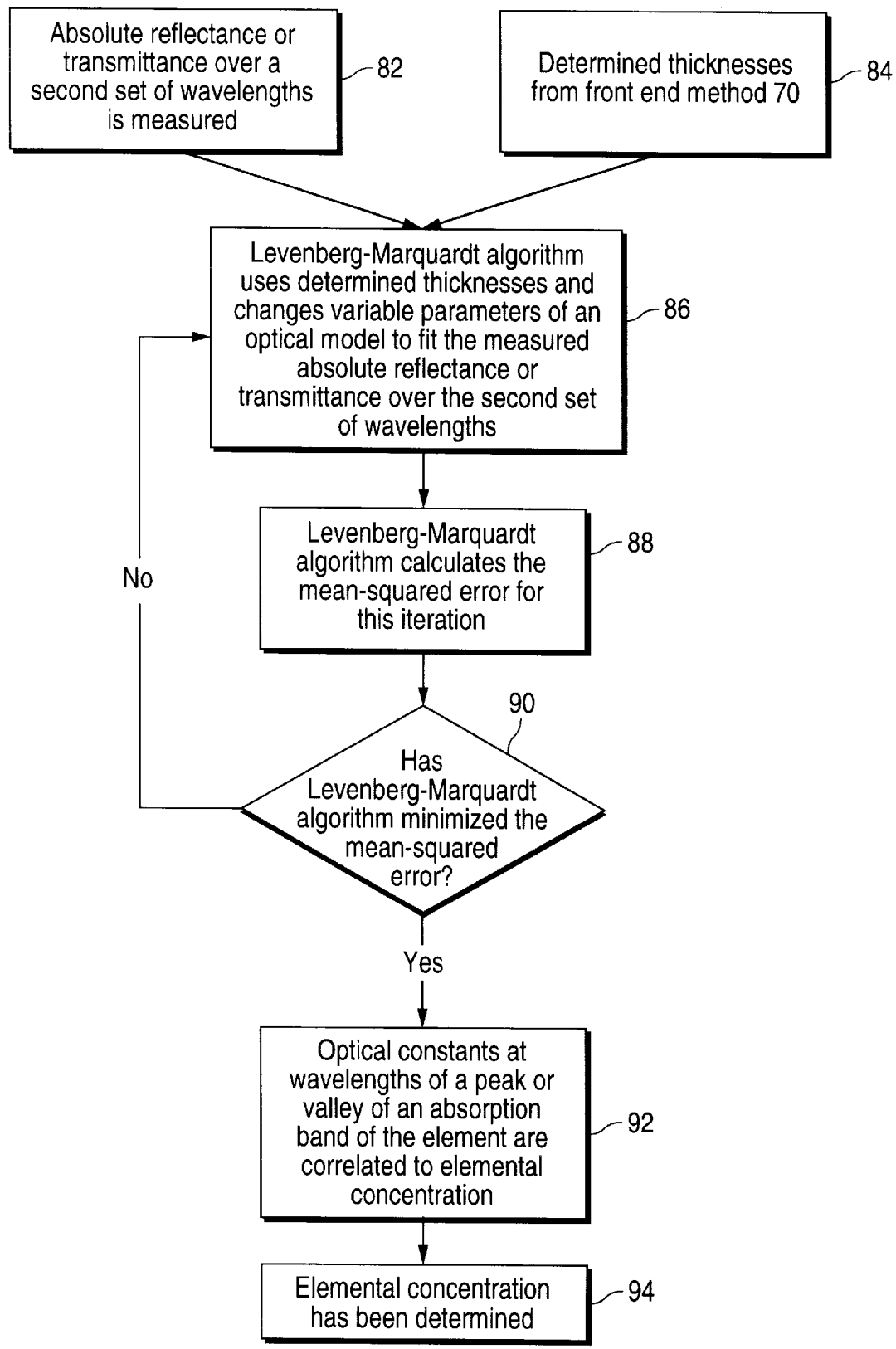
FIG. 11 is a flow chart of a method used to determine the concentration of the element of interest in thin films in accordance with one embodiment of the present invention.

FIG. 11 illustrates one embodiment of back end method 71 by which integrated optical measuring instrument 1 determines one element's concentration in one film layer of sample substrate 38. This embodiment relates optical constants of the film layer at the wavelength of a peak or valley of an absorption band of an element to that element's concentration.

In step 82, FTIR spectrometer 6 measures absolute reflectance or transmittance from area 37 over a second set of wavelengths, e.g., IR spectral range. In step 84, microprocessor 8 recalls the previously determined film layer thicknesses from front end method 70 described above and in FIG. 5. Of course, if desired, the measurement for front end method 70 and back end method 71 may be taken at approximately the same time. In steps 86, 88, and 90, microprocessor 8 applies the Levenberg-Marquardt algorithm to fit the optical model of sample substrate 38 to the measured absolute reflectance or transmittance over the second set of wavelengths.

As previously discussed, the Levenberg-Marquardt algorithm works as follows. In step 86, the Levenberg-Marquardt algorithm selects values for variable parameters in the optical model, e.g., optical constants of the film layers over the second set of wavelengths, to calculate a theoretical absolute reflectance or transmittance over the second set of wavelengths. Note that the Levenberg-Marquardt algorithm does not need to select values for film layer thicknesses because they are determined by front end method 70. In step 88, the Levenberg-Marquardt algorithm compares the theoretical absolute reflectance or transmittance to the measured absolute reflectance or transmittance to determine the mean-squared error. In step 90, if the Levenberg-Marquardt algorithm has minimized the mean-squared error, the values for the variable parameters, e.g., optical constants of the film layers over the second set of wavelengths, are deemed the actual physical values of those parameters. If the Levenberg-Marquardt algorithm has not minimized the mean-squared error, steps 86, 88 and 90 are repeated.

Parametric dispersion models representing the optical constants of the film layers may again be used in the optical model. As previously discussed, parametric dispersion models help the Levenberg-Marquardt algorithm to produce a unique solution for the variable parameters. Parametric dispersion models that describe optical constants for a wide range of materials are well understood by those of ordinary skill in the art. For example, the previously discussed Lorentz oscillator dispersion model may be used.

In step 92, microprocessor 8 relates optical constants of a film layer at the wavelength of a peak or valley of an absorption band of the element to the concentration of the element in that film layer. The relationship between the optical constants in the absorption band and the element's concentration must be previously determined with calibration samples with known concentrations of the element. To determine this relationship, methods described above and in FIGS. 5 and 11 are used to determine the optical constants of the film layers of the calibration samples. A function that correlates the determined optical constants at the wavelength of the peak or valley of the absorption band of the element to the known concentration of the element is then determined by curve fitting methods well understood by those of ordinary skill in the art.

Alternatively, the dispersion models are used to determine the concentration of the element in the film layer. For example, in the Lorentz oscillator dispersion model, the amplitude of the oscillator describing the absorption band can be correlated directly to the concentration. Alternatively, the imaginary part of the dielectric function at a given wavelength is directly proportional to the energy absorbed per unit volume by the film at that wavelength, such that the value of the imaginary part of the dielectric function at the absorption band peak may also be correlated to the concentration of the element. To determine this relationship, methods described above and in FIGS. 5 and 11 are used to determine the constants of the parametric dispersion models, specifically the amplitudes of the oscillators describing the absorption band or the imaginary parts of the dielectric functions at the absorption band peak, from the calibration samples. A function that correlates the amplitude of the oscillator describing the absorption band, or the imaginary part of the dielectric function at the absorption band peak, to the known concentration of the element is then determined by curve fitting methods well understood by those of ordinary skill in the art.

While the present disclosure discusses the use of a FTIR spectrometer that measures absolute reflectance or transmittance over the second set of wavelengths, it should be understood that an embodiment of the present invention may also use spectral analysis instruments that measure reflectance, transmittance, ellipsometric parameters, or any combination thereof, over the second set of wavelengths. Those of ordinary skill in the art will understand that additional measured spectral data helps the Levenberg-Marquardt algorithm to produce unique solutions to the variable parameters of the optical model.

Furthermore, while the present disclosure discusses the determination of elemental concentration, it should be understood that the methods described above and throughout this disclosure are applicable to the measurement of the density of a chemical bond in the film. One skilled in the art will understand that absorption bands in spectral measurements over the IR spectral range are caused by the absorption of electromagnetic energy by chemical bonds between elements. The type of a chemical bond and the masses of the elements bonded determine where an absorption band occurs in the IR spectral range while the density of the chemical bond determines the amount of electromagnetic energy absorbed. Thus, the wavelength at an absorption band can be related to the type of a chemical bond between specific elements and spectral measurements at that wavelength, such as optical constants, can be related to the density of the chemical bond. In fact, the measurement of an element's concentration is a measurement of a specific type of a chemical bond—the bond between the element of interest and the host material in the film.

Figure 12:
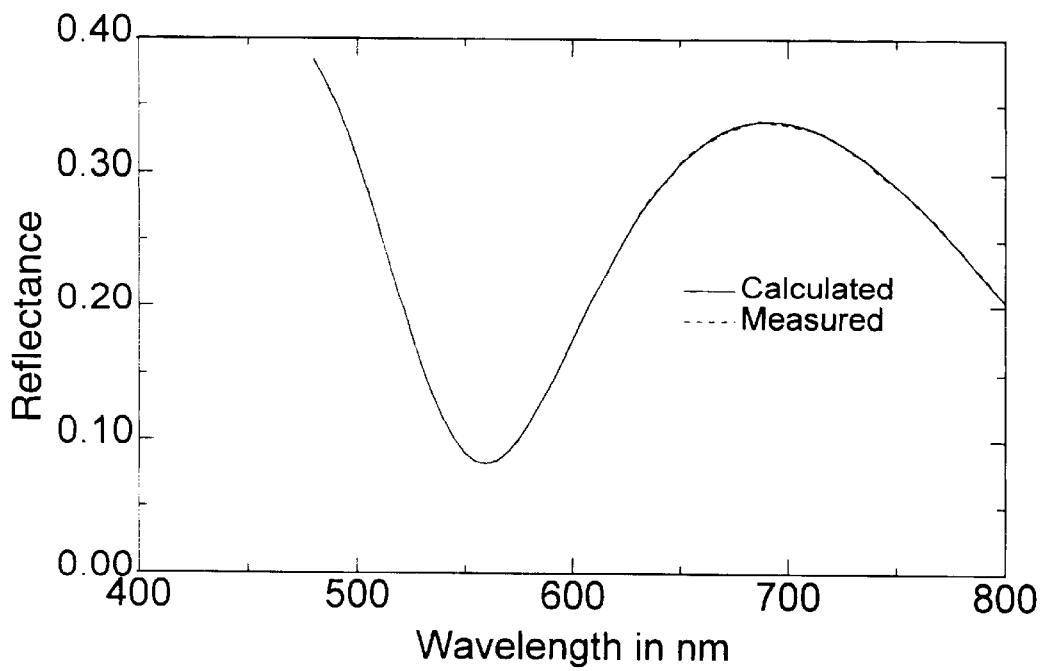
FIG. 12 is a graph of the measured absolute reflectance and the calculated (theoretical) absolute reflectance of a sample silicon dioxide thin film doped with phosphorus over the first set of wavelengths.
Figure 13:
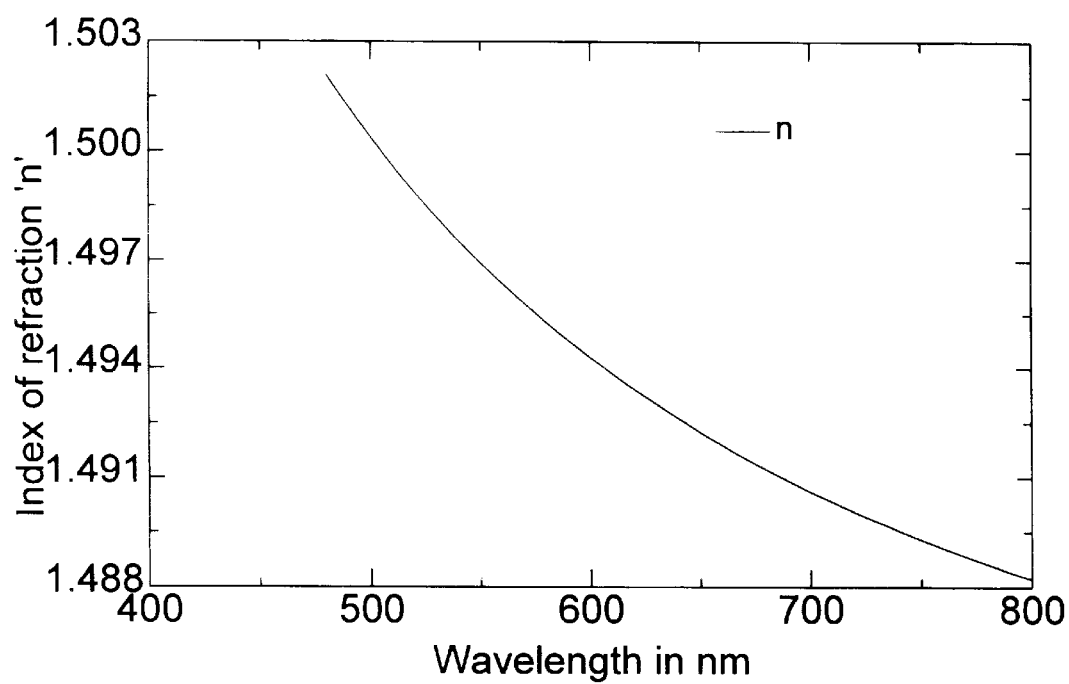
FIG. 13 is a graph of the determined index of refraction n of the sample silicon dioxide thin film doped with phosphorus.

An embodiment including front end method 70 described above and in FIG. 5 and back end method 71 described above and in FIG. 11 is demonstrated by the following example, wherein the film layer thicknesses, optical constants, and phosphorus concentrations are determined for a silicon dioxide ($SiO_2$) thin film that has been doped with phosphorus. The film layer thickness and optical constants over the first set of wavelengths are determined by front end method 70 described above and in FIG. 5. In this example, front end method 70 uses only DUV-NIR reflectometer 2 and not VIS ellipsometer 4. DUV-NIR reflectometer 2 is used to measure absolute reflectance at normal incidence over a spectral range of 480 to 800 nm. Assuming the extinction coefficient k of the optical constants to be zero at this spectral range, microprocessor 8 uses the Levenberg-Marquardt algorithm to determine a film layer thickness and index of refraction n that produce theoretical absolute reflectance from the optical model that best match the measured absolute reflectance. FIG. 12 shows the measured and best-fit theoretical absolute reflectance. The best-fit theoretical absolute reflectance is produced by a silicon dioxide film thickness of 466.1 nm and the index of refraction n over 480 to 800 nm shown in FIG. 13.

Figure 14:
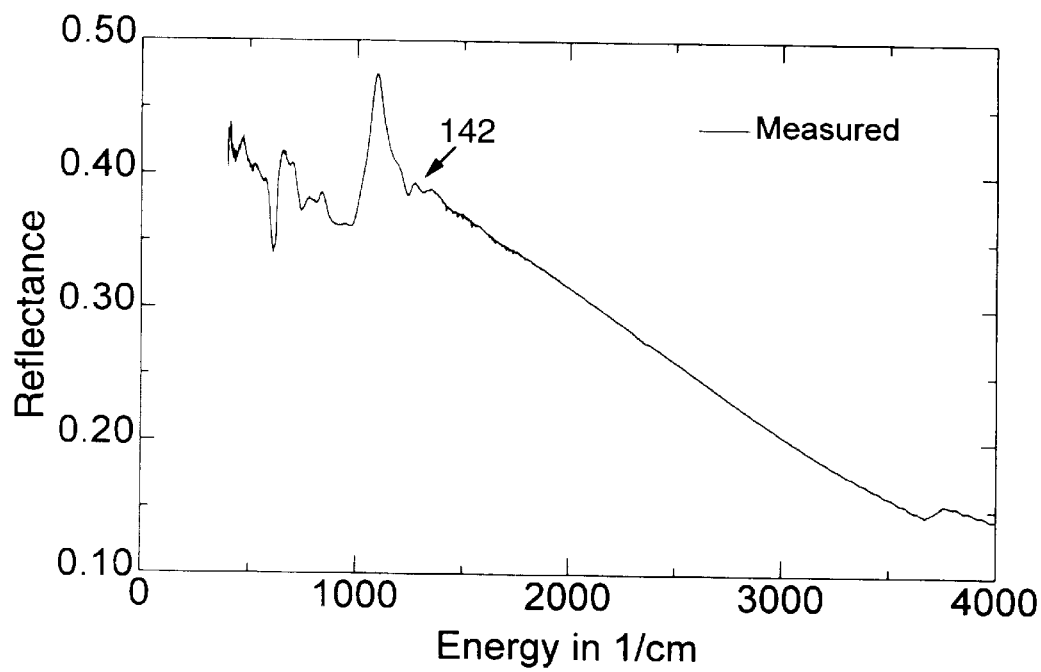
FIG. 14 is a graph of the measured absolute reflectance of the sample silicon dioxide thin film over the second set of wavelengths (shown in wavenumbers $cm^{-1}$), where the features due to phosphorus are indicated by arrow 142.
Figure 15:
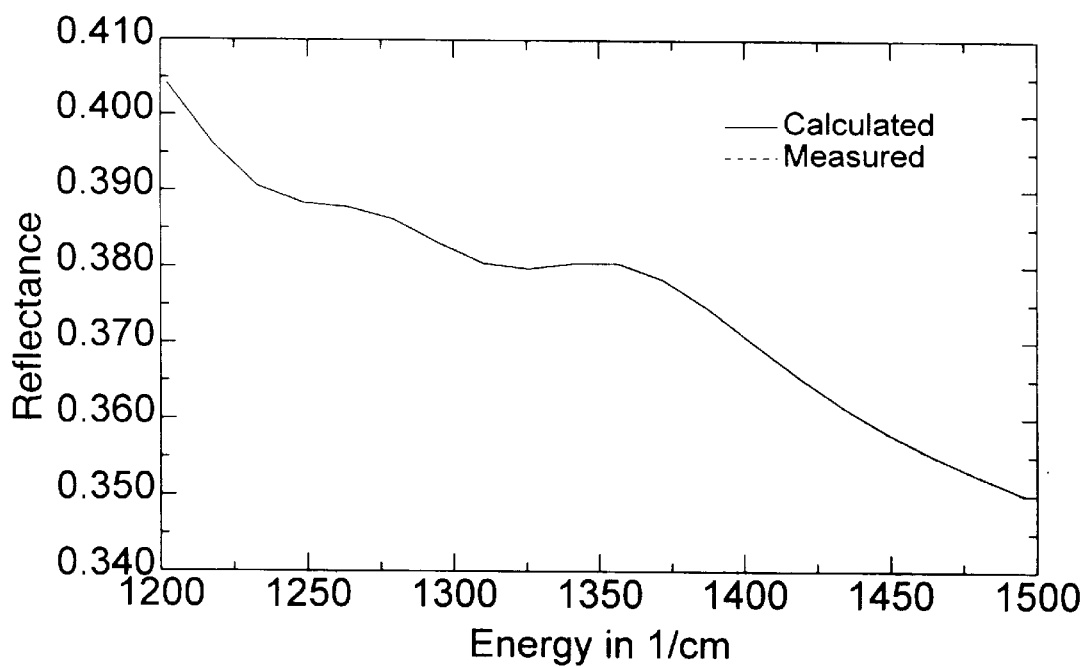
FIG. 15 is a graph of the measured absolute reflectance and the calculated (theoretical) absolute reflectance of a sample silicon dioxide thin film doped with phosphorus over a subset of the second set of wavelengths (shown in wavenumbers $cm^{-1}$).
Figure 16:
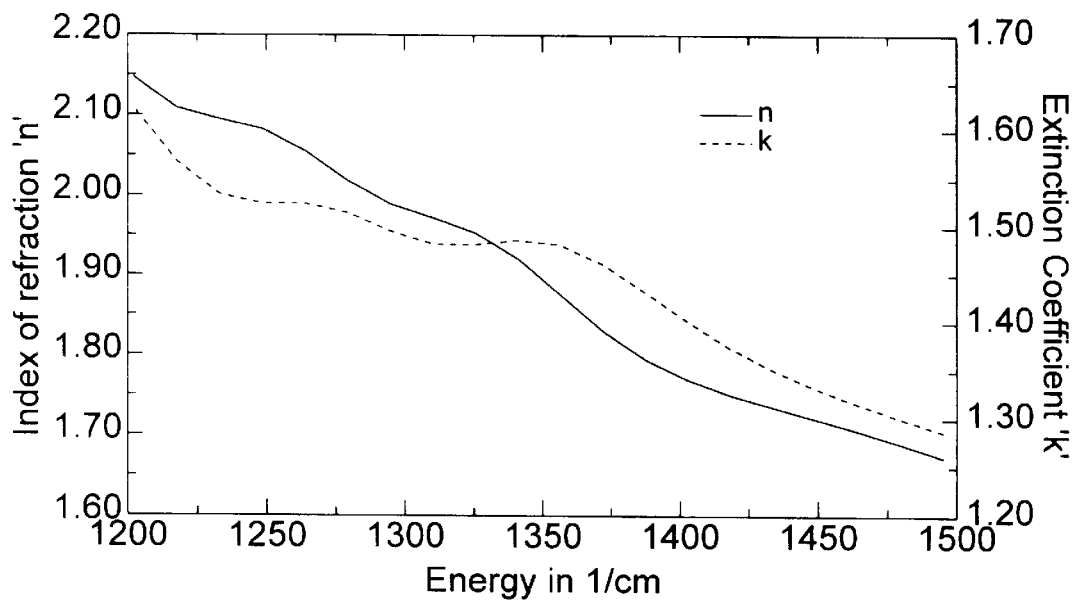
FIG. 16 is a graph of the determined optical constants of the sample silicon dioxide thin film doped with phosphorus over the subset of the second set of wavelengths (shown in wavenumbers $cm^{-1}$).

FTIR reflectometer 6 then measures the absolute reflectance at near-normal incidence over the IR spectral region. The measured absolute reflectance is shown in FIG. 14, where the absorption feature caused by phosphorus is shown by an arrow 142. Please note that wavelengths in many figures are shown as wavenumbers $cm^{-1}$, i.e., the number of waves within one centimeter. Using the determined film layer thickness, microprocessor 8 applies the Levenberg-Marquardt algorithm to determine optical constants (both n and k) that produce theoretical IR absolute reflectance from the optical model that best matches the measured IR absolute reflectance. In this example, the optical constants are represented a Lorentz oscillator model (Equ. 2) consisting of five separate oscillators that describe the optical absorption of the film. Thus, the Levenberg-Marquardt algorithm systematically varies fifteen variable parameters (each oscillator model has three parameters) to find their best-fit values. FIG. shows the measured and best-fit theoretical absolute reflectance over a selected spectral region. The best-fit theoretical absolute reflectance is produced by optical constants shown in FIG. 16.

Figure 17:
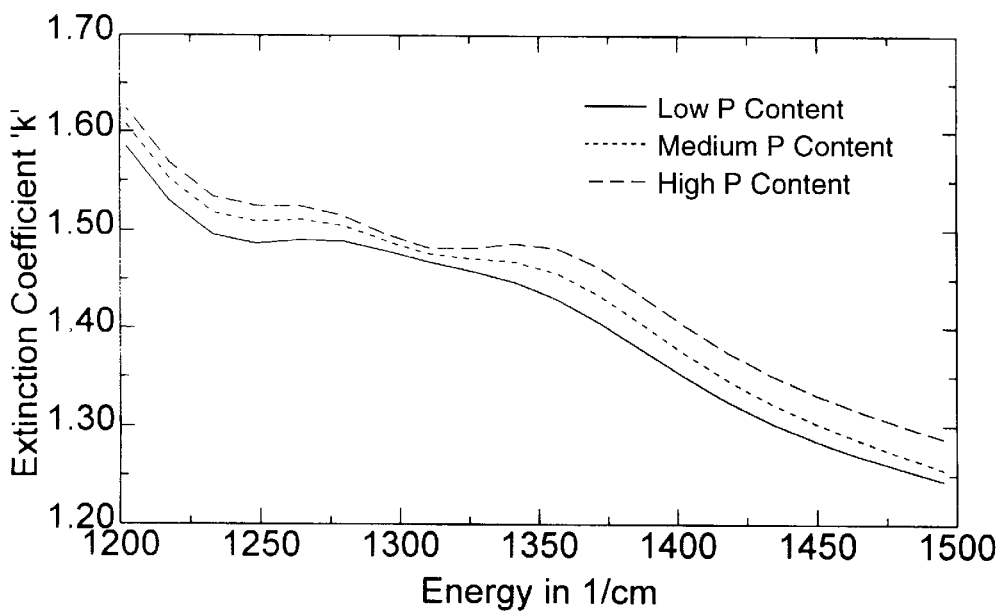
FIG. 17 is a graph of the extinction coefficient k of three silicon dioxide thin films doped with varying concentrations of phosphorus over the subset of the second set of wavelengths (shown in wavenumbers $cm^{-1}$).

FIG. 17 shows the spectra of the extinction coefficient k of the optical constants for three silicon dioxide films of similar thickness and differing phosphorus concentrations. As FIG. 17 demonstrates, the optical constants for the silicon dioxide films in the IR spectral range change strongly with phosphorus concentration in the film and can therefore be correlated to phosphorus concentration via a simple empirical relationship:

$$\% P = f(n(\lambda), k(\lambda)),\quad \text{Equ. 3}$$

where % P is the phosphorus concentration in the film, $n(\lambda)$ and $k(\lambda)$ are the IR optical constants of the film, f(n,k) is a simple mathematical function of the optical constants, and $\lambda$ is a wavelength at a peak or valley of an absorption band in the IR spectral region caused by the element of interest. The function f(n,k) is solved from the optical constants determined from calibration films with known concentrations. For the specific example at hand, the calibration function derived from calibration samples is as follows:

$$\% P = A_0 + B_0 * k(1350\ cm^{-1})\quad \text{Equ. 4}$$

with $A_0$ is 0.023907, $B_0$ is 1.340018, and $\lambda$ is 1350 $cm^{-1}$.

Figure 18A:
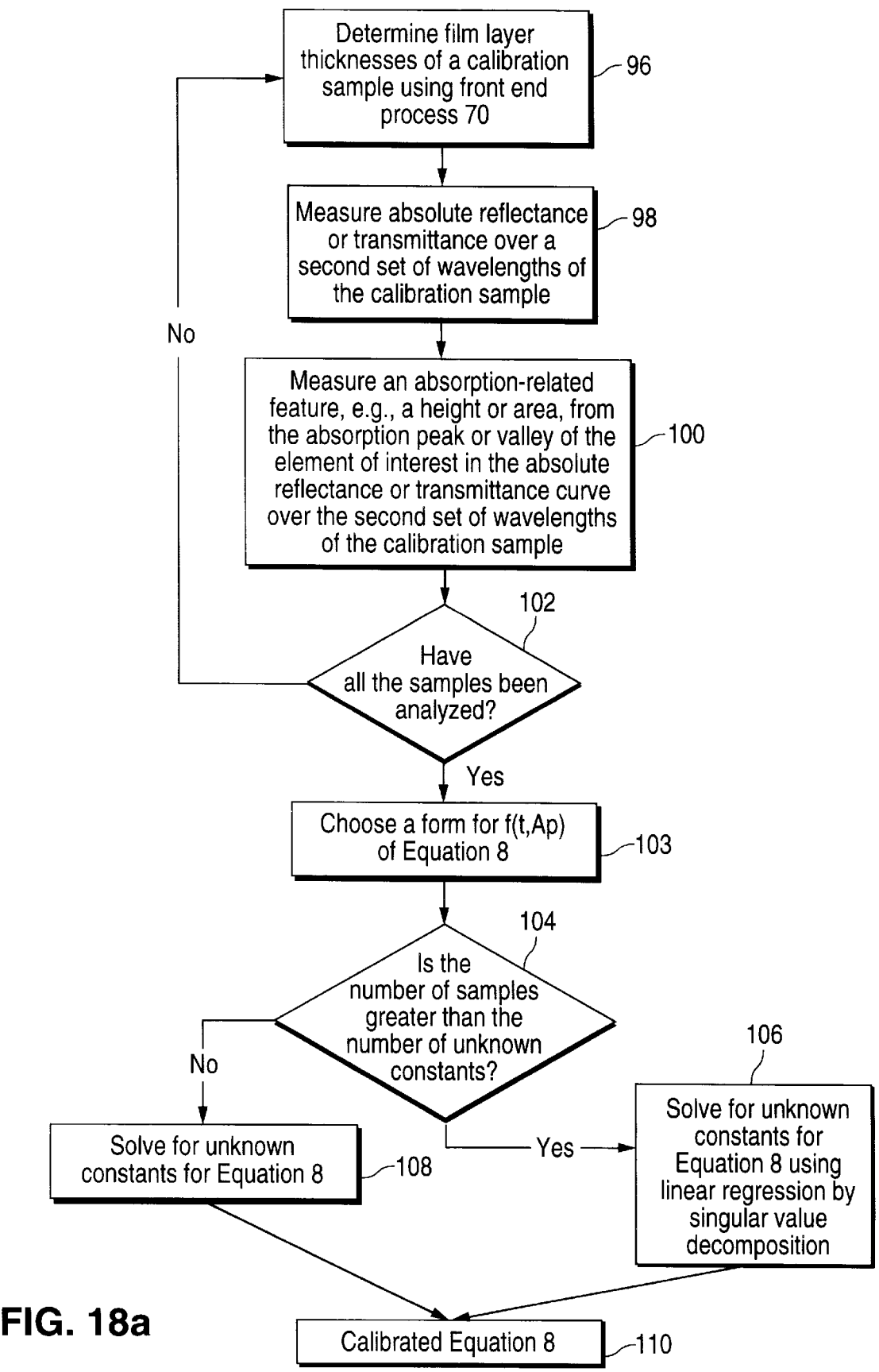
FIG. 18a is a calibration flow chart for a method used to determine the concentration of the element of interest in thin films in accordance with another embodiment of the present invention.
Figure 18B:
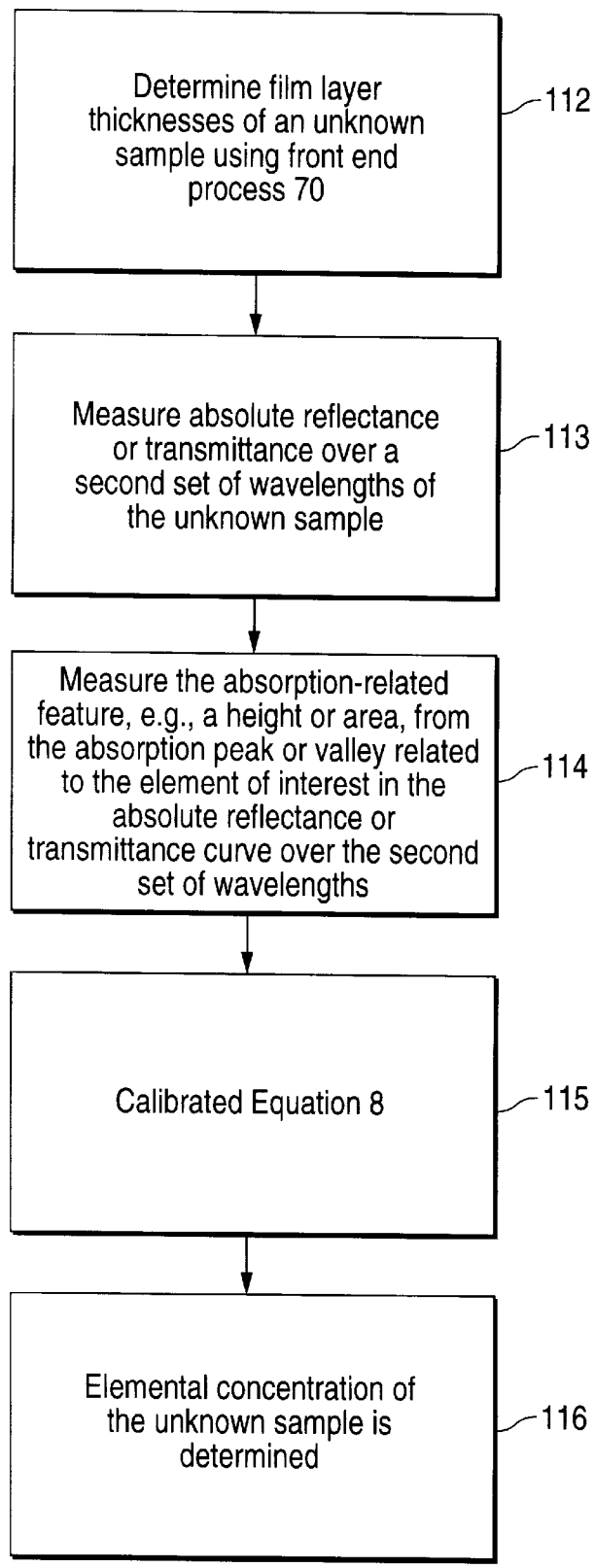

FIGS. 18a and 18b illustrates another embodiment of back end method 71 by which integrated optical measuring instrument 1 determines an element's concentration in a film layer of sample substrate 38. This embodiment relies more directly on the use of a set of calibration samples with known concentration of the element to determine a relationship among the film layer thickness, a measurable absorption-related feature, and the element's concentration. The absorption-related feature can be the height or area of an absorption peak or valley in the IR absolute reflectance or transmittance curve, or in a first or higher order derivative of the absolute reflectance or transmittance curve. For example, an integrated area from 950 to 1100 $cm^{-1}$ in the IR reflectance of fluorinated silicon dioxide films shown in FIGS. 20 to 23 may be measured as the absorption-related feature for fluorine concentration calculations.

One way to determine the relationship among the film layer thickness, the measurable absorption-related feature, and the element's concentration is to assume that the element's concentration is a polynomial function of the absorption-related feature, and the intercept and slope of this function are polynomial functions of the film layer thickness. Denoting the concentration as a quadratic function of the absorption-related feature, and the intercept and slope of this function as quadratic functions of the film layer thickness, the concentration of the element is given as follows:

$$C = (c_1 + c_2 t + c_3 t^2) + (c_4 + c_5 t + c_6 t^2) A_p + (c_7 + c_8 t + c_9 t^2) A_p^2,\quad \text{Equ. 5}$$

where C is the concentration of the element, $c_1$ to $c_9$ are constants for the element, t is the film layer thickness, and $A_p$ is the absorption-related feature value. To solve the constants $c_1$ to $c_9$, the number of calibration samples with known concentrations of the element must be at least equal to the number of constants to be solved. Note that Equ. 5 can be simplified with some loss of flexibility by setting any of the constants to zero. For example, setting $c_3$, $c_6$, and $c_7$ to $c_9$ to zero, Equ. 5 becomes:

$$C = (c_1 + c_2 t) + (c_4 + c_5 t) A_p.\quad \text{Equ. 6}$$

Alternatively, Equ. 5 can be generalized by adding additional terms to the polynomials of the film thickness t and absorption-related feature $A_p$. For example, adding additional polynomials of $t^3$ and $A_p^3$, Equ. 5 becomes:

$$C = (C_1 + c_2 t + c_3 t^2 + c_4 t^3) + (c_5 + c_6 t + c_7 t^2 + c_8 t^3) A_p + (c_9 + c_{10} t + c_{11} t^2 + c_{12} t^3) A_p^2 + (c_{13} + c_{14} t + c_{15} t^2 + c_{16} t^3) A_p^3,\quad \text{Equ. 7}$$

where $c_1$ through $c_{16}$, are constants for the element. Lastly, Equ. 5 can be written in a considerably more general form as follows:

$$C(t, A_p) = \sum_{i=1}^{N} c_i \cdot f_i(t, A_p),\quad \text{Equ. 8}$$

where $c_i$ represents the constants, N is the total number of constants and the minimum number of calibration samples necessary to solve the constants, and $f_i(t, A_p)$ is a general function. It is important to understand that function $f_i(t, A_p)$ may take any form, such as those described above, as long as concentration is a linearly function of the constants.

If the number of calibration samples exceeds the number of unknown constants and the conditions stated by Equ. 6 are met, the constants can be determined by linear regression using singular value decomposition. Linear regression by singular value decomposition is well understood by those of ordinary skill in the art and is further described in "Numerical Recipes in C" by W. H. Press, B. P. Fannery, S. A. Teukolsky, and W. T. Vetterling, published by Cambridge University Press (1992), which was previously incorporated by reference. Preferably, a greater number of calibration samples than constants is used to over-determine the calibration constants.

Thus, integrated optical measuring instrument 1, more specifically microprocessor 8, must first be calibrated using calibration samples with known concentrations of the element of interest. FIG. 18a is a flow chart for calibrating microprocessor 8. In step 96, film layer thicknesses of a first calibration sample are determined from front end method 70 described above and in FIG. 5. In step 98, FTIR spectrometer 6 measures the calibration sample's absolute reflectance or transmittance over the second set of wavelengths. In step 100, microprocessor 8 determines the calibration sample's absorption-related feature value, e.g., a height or an area from the absorption peak or valley related to the element, in the absolute reflectance or transmittance curve over the second set of wavelengths. Steps 96, 98, and 100 are repeated for each calibration sample. In step 103, the user must decide what form of $f(t, A_p)$ of Equ. 8 he or she wishes to apply. For example, one of Equ. 5 to 7 may be chosen. In step 104, if the number of calibration samples is greater than the number of constants, microprocessor 8 will employ linear regression by singular value decomposition in step 106 to solve for the constants. If the number of calibration samples is equal to the number of constants, microprocessor 8 will determine the constants in step 108 by inserting the determined film layer thicknesses, the absorption-related feature values, and the known elemental concentrations into a system of linear equations created by Equ. 8 and solving the system of linear equations.

Once a set of constants for a specific element is determined, microprocessor 8 can use Equ. 8 to calculate the concentration of the element in a film layer of an unknown sample by determining the film M-7161 US value from the IR absolute reflectance or transmittance. FIG. 18*b* is the flow chart of the steps used to predict the concentration of the element. In step 112, film layer thicknesses of sample substrate 38 is determined by front end method 70 described above and in FIG. 5. In step 113, FTIR spectrometer 6 measures the IR absolute reflectance or transmittance over the second set of wavelengths. In step 114, microprocessor 8 determines the absorption-related feature value from the measured absolute reflectance or transmittance curve over the second set of wavelengths, e.g., a height or an area from the absorption peak or valley related to the element. In step 115, microprocessor 8 solves for the element's concentration in each film layer via Equ. 8.

While the present disclosure discusses the determination of elemental concentration, it should be understood that the methods described above and throughout this disclosure are applicable for the measurement of the density of a chemical bond in the film. As previously discussed, one skilled in the art will understand that IR spectral measurements can be related to the type of a chemical bond between specific elements and the density of the chemical bond.

Furthermore, while the present disclosure discusses the use of integrated optical measuring instrument 1, one skilled in the art will understand that the methods described above and in FIGS. 18*a* and 18*b* can be applied with separate optical measuring instruments. For example, a first optical measuring instrument can be used to determine film layer thickness and a second optical measuring instrument can be used to determine the value of the absorption-related feature in the IR reflectance or transmittance. These values can then be input into a computer program to determine elemental concentration.

Figures 19, 20:
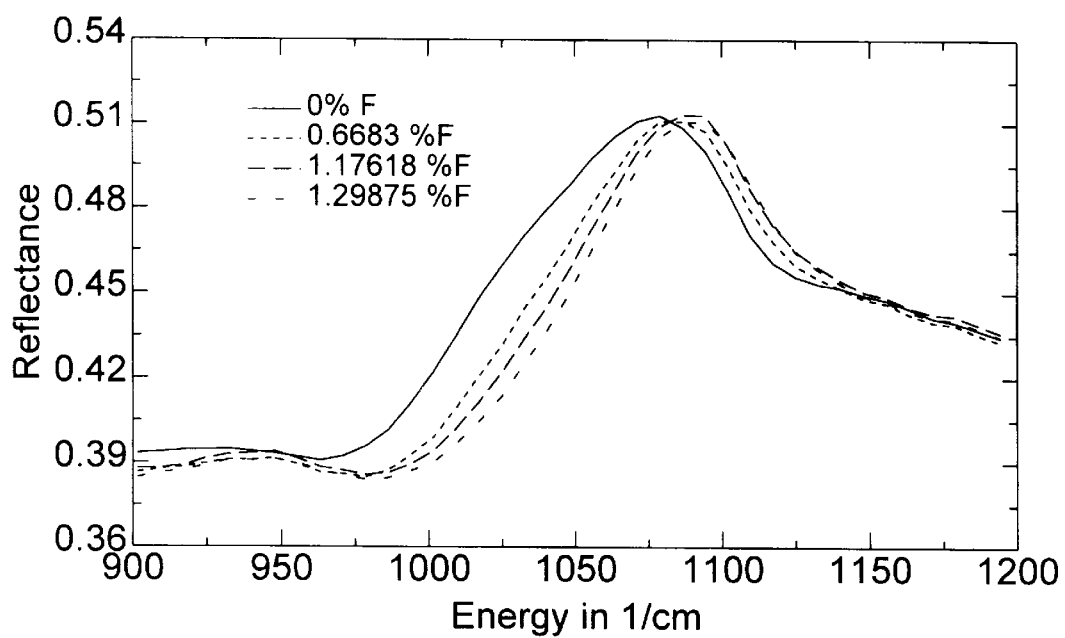
FIG. 19 is a table containing the determined film layer thicknesses and the known fluorine concentrations of fluorinated silicon dioxide calibration samples.
FIG. 20 is a graph of the measured absolute reflectance over multiple wavelengths (shown in wavenumbers $cm^{-1}$) of four fluorinated silicon dioxide calibration samples with film layer thicknesses of approximately 3500 Å (Angstroms).
Figure 21:
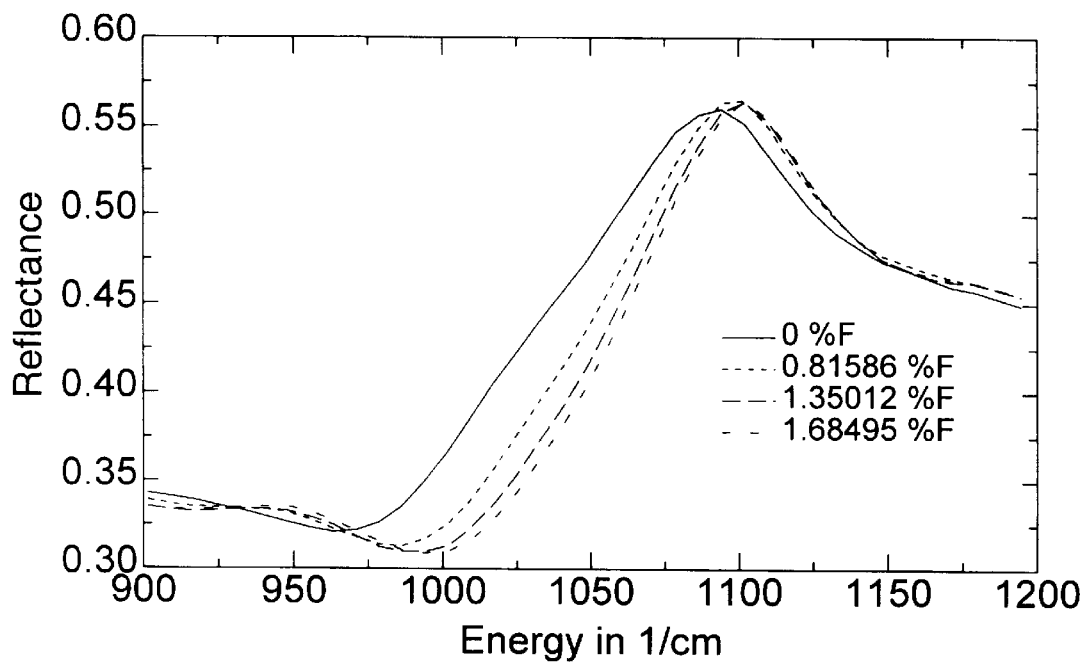
FIG. 21 is a graph of the measured absolute reflectance over multiple wavelengths (shown in wavenumbers $cm^{-1}$) of another four fluorinated silicon dioxide calibration samples with film layer thicknesses of approximately 6200 Å.
Figure 22:
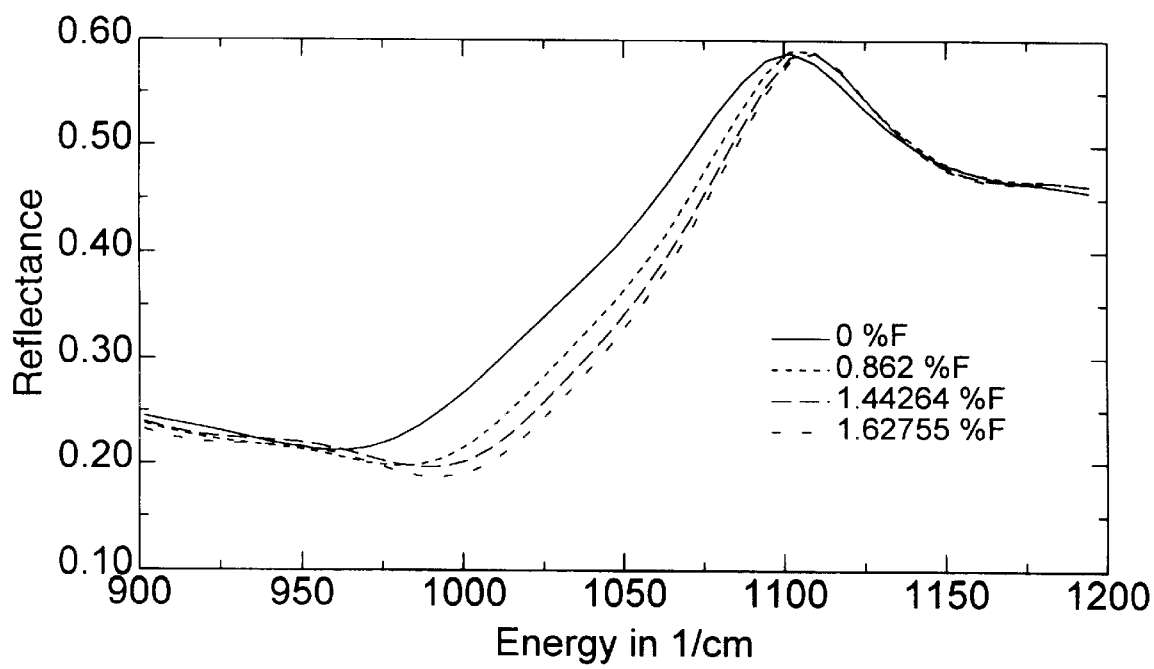
FIG. 22 is a graph of the measured absolute reflectance over multiple wavelengths (shown in wavenumbers $cm^{-1}$) of another four fluorinated silicon dioxide calibration samples with film layer thicknesses of approximately 9500 Å.
Figures 23, 24:
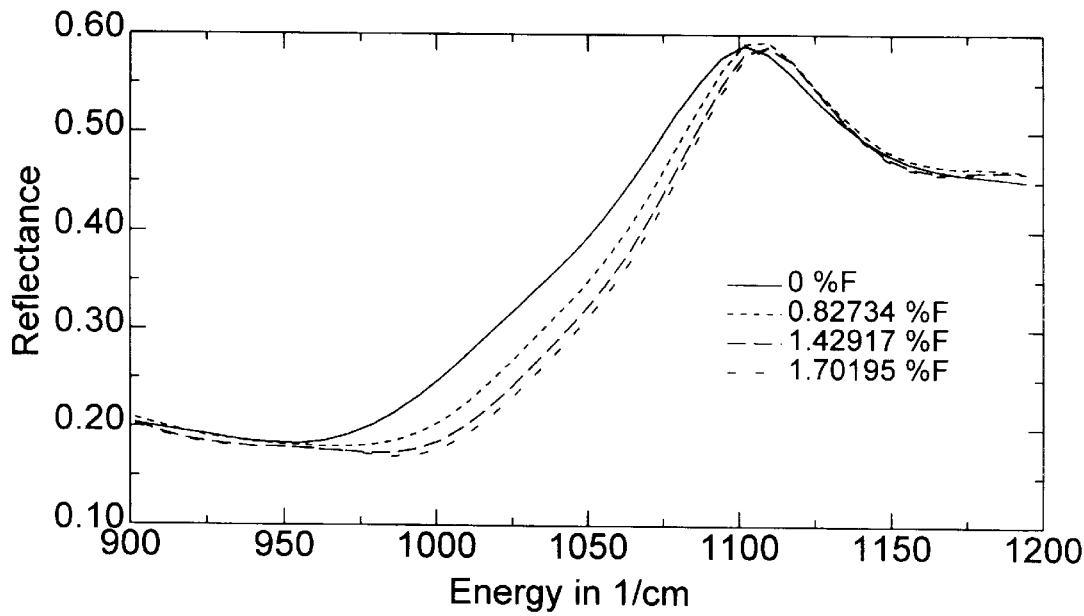
FIG. 23 is a graph of the measured absolute reflectance over multiple wavelengths (shown in wavenumbers $cm^{-1}$) of another four fluorinated silicon dioxide calibration samples with film layer thicknesses of approximately 11,500 Å
FIG. 24 is a table containing the determined film layer thicknesses, the measured absorption-related feature values (integrated area from 950 to 1100 $cm^{-1}$), and the known fluorine concentrations of the fluorinated silicon dioxide calibration samples.
Figure 25:
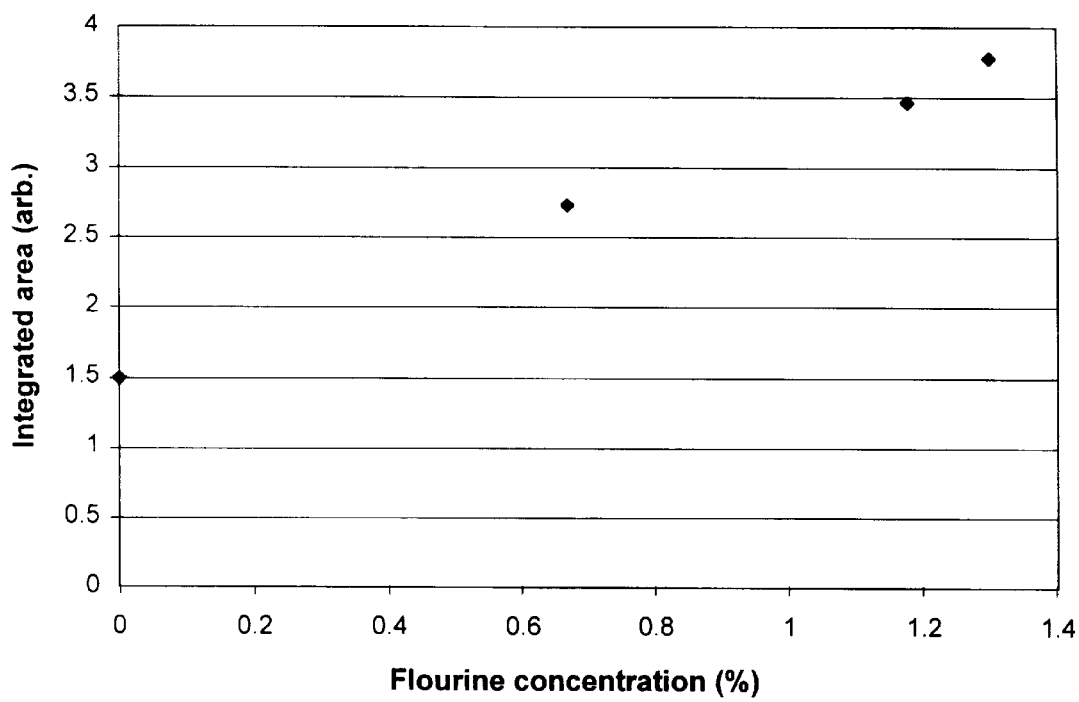
FIG. 25 is a graph of the measured absorption-related feature values against the known fluorine concentrations of four fluorinated silicon dioxide calibration samples with film layer thicknesses of approximately 3500 Å.
Figure 26:
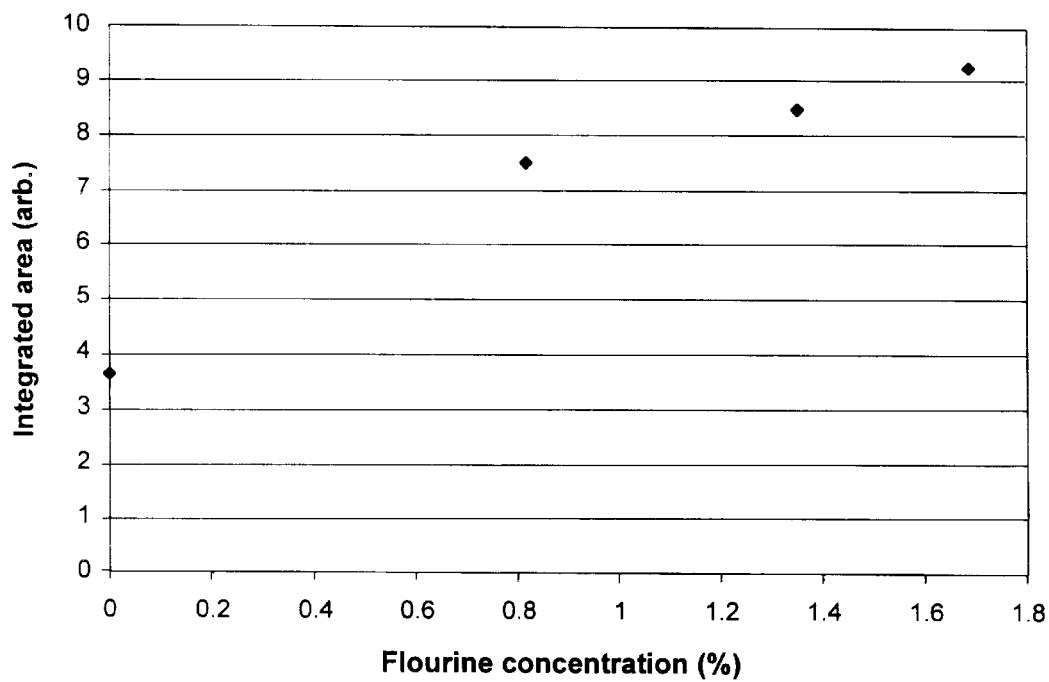
FIG. 26 is a graph of the measured absorption-related feature values against the known fluorine concentrations of four fluorinated silicon dioxide calibration samples with film layer thicknesses of approximately 6200 Å.
Figure 27:
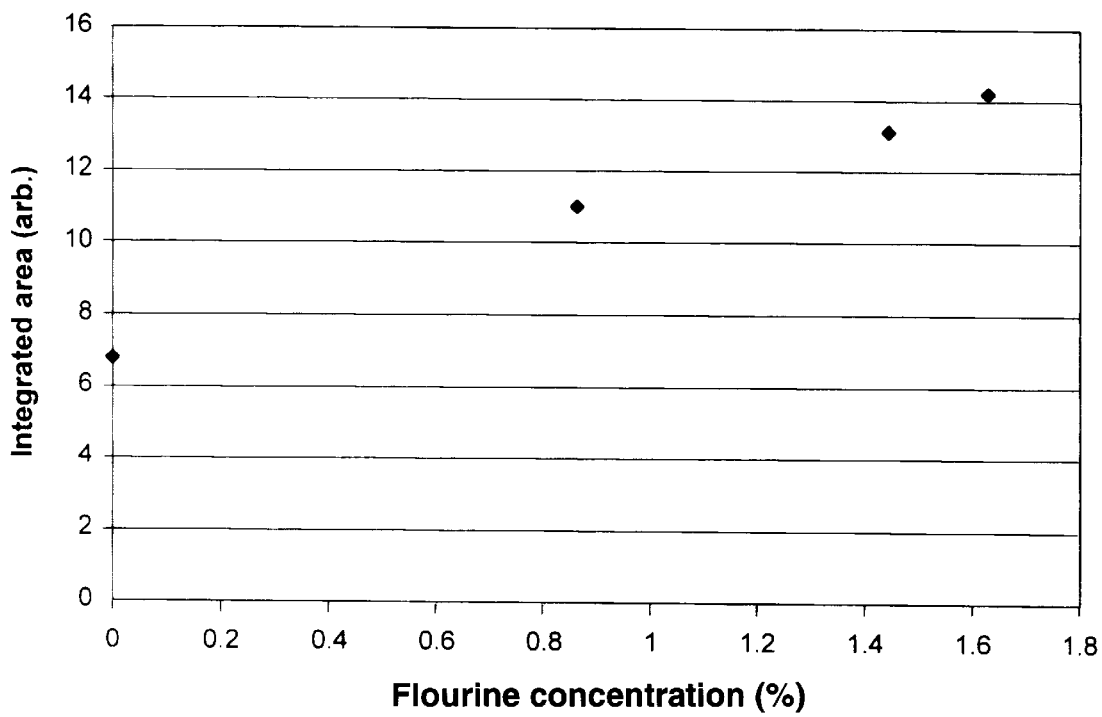
FIG. 27 is a graph of the measured absorption-related feature values against the known fluorine concentrations of four fluorinated silicon dioxide calibration samples with film layer thicknesses of approximately 9500 Å.
Figure 28:
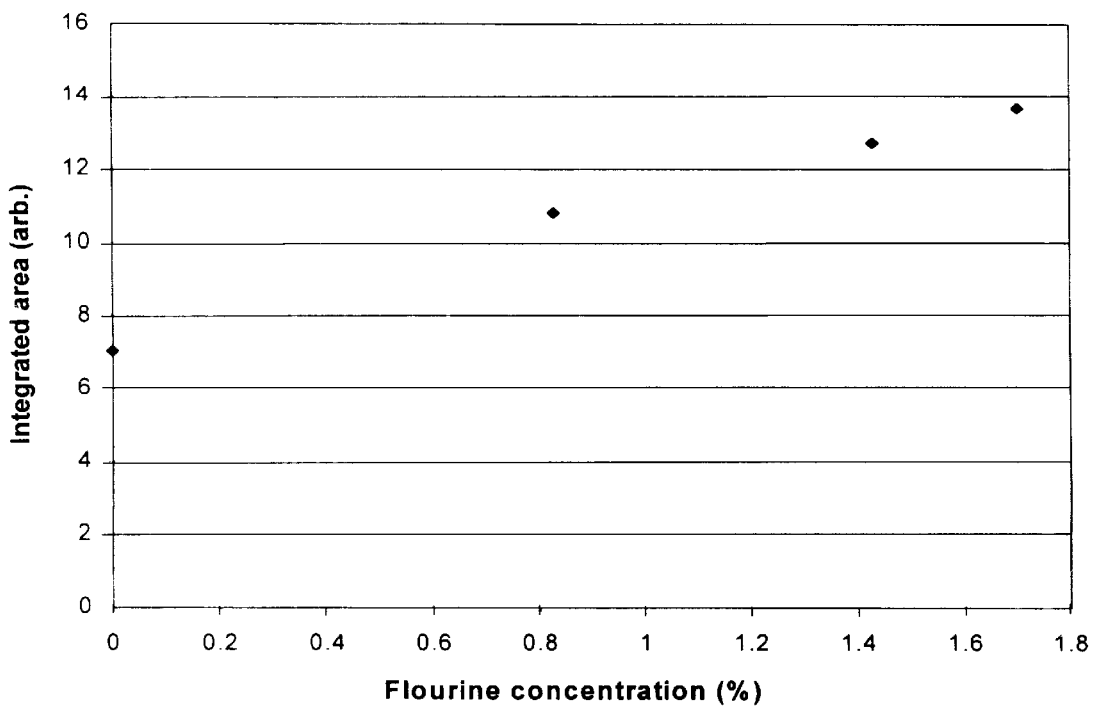
FIG. 28 is a graph of the measured absorption-related feature values against the known fluorine concentrations of four fluorinated silicon dioxide calibration samples with film layer thicknesses of approximately 11,500 Å.

An embodiment comprising front end method 70 described above and in FIG. 5 and back end method 71 described above and in FIGS. 18*a* and 18*b* is demonstrated by the following example. In this example, sixteen calibration samples of fluorinated silicon dioxide thin films with varying film layer thicknesses and known fluorine concentrations are used. Following the flow chart of FIG. 18*a*, the film layer thicknesses of the calibration samples are first determined by front end method 70 described above and in FIG. 5. FIG. 19 provides a table containing the determined film layer thicknesses and the known fluorine concentrations of the calibration samples. Next, the IR absolute reflectances of the calibration samples are measured. FIGS. 20 to 23 illustrate the absolute IR reflectances of the calibration samples, where calibration samples with similar film layer thicknesses are grouped together. Microprocessor 8 then measures an absorption-related feature from the IR absolute reflectances. In this example, the integrated area from 950 to 1100 cm$^{-1}$ of the absorption band of fluorine is chosen as the absorption-related feature. FIG. 24 provides a table containing the film layer thicknesses, the integrated area values, and the concentrations of fluorine. FIGS. 25 to 28 present graphs of the values of the absorption-related feature versus the fluorine concentrations of calibration samples, where calibration samples with similar film layer thicknesses are grouped together. FIGS. 25 to 28 clearly demonstrate a correlation between the absorption-related feature, film layer thickness, and concentration of fluorine. At this point, Equ. 5 is chosen to determine the fluorine concentrations and microprocessor 8 uses linear regression by singular value decomposition to solve the constants of Equ. 5 because there are more calibration samples (16) than constants (9). The result is as follows:

$$\% \ F = (-0.3457 - 0.002783*t + 2.148 \times 10^{-6}*t^2) + (1.485 - 0.002696*t + 1.271 \times 10^{-6}*t^2)A_p + (-0.0479 + 1.119 \times 10^{-4}*t - 5.522 \times 10^{-8}*t^2)A_p^2 \quad \text{Equ. 9}$$

Equ. 9 can now be used to determine fluorine concentration of thin films. To determine fluorine concentrations of thin films, the film layer thickness of an unknown sample is first determined. Next, IR absolute reflectance of the unknown sample is measured and the value of the absorption-related feature, i.e., integrated area from 950 to 1100 cm$^{-1}$, is determined. The concentration of fluorine is then calculated using Equ. 9 with the film layer thicknesses and absorption-related feature value.

Figure 29A:
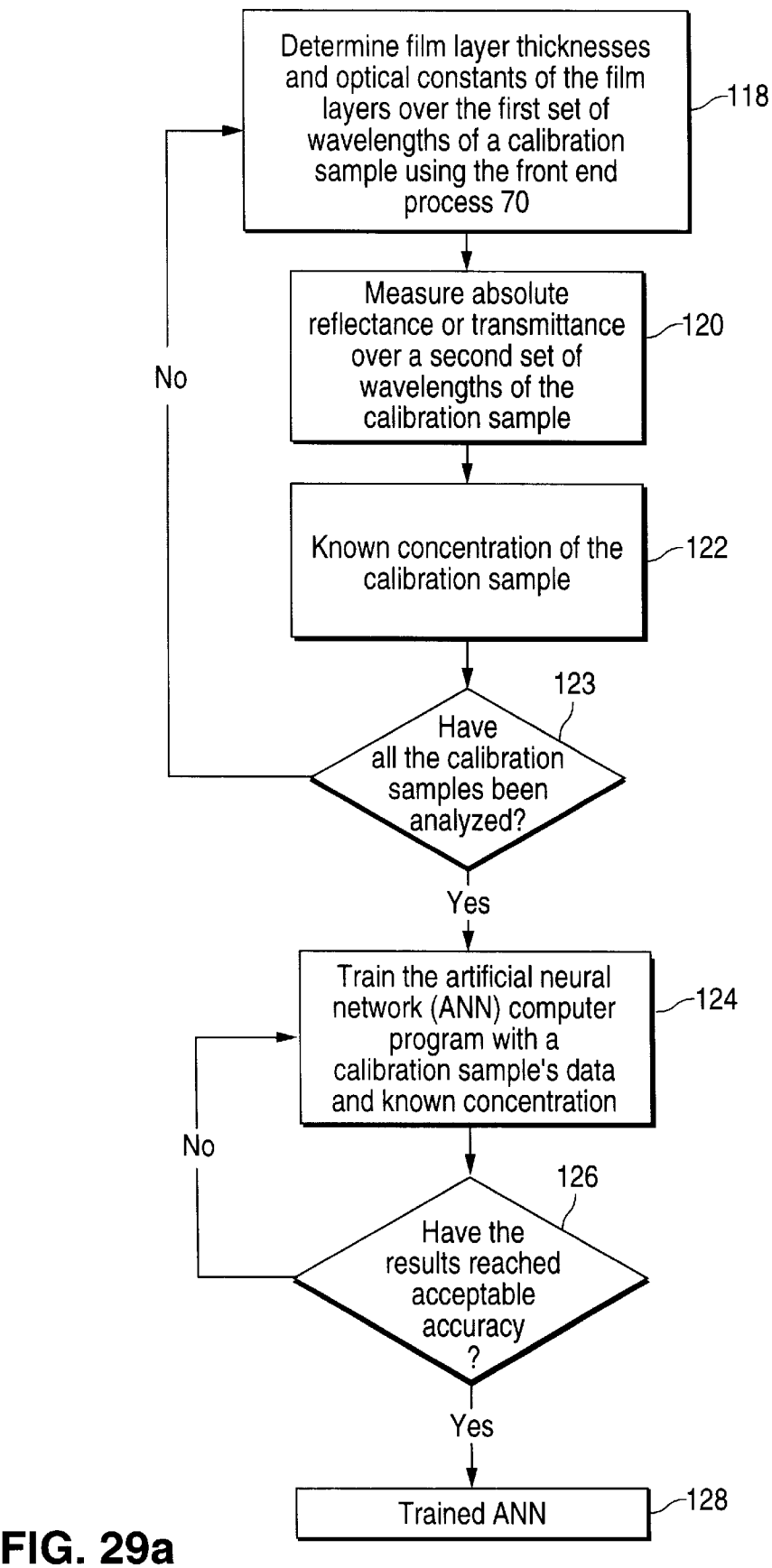
FIG. 29a is a calibration flow chart of a method used to determine the concentration of the element of interest in thin films in accordance with yet another embodiment of the present invention.
Figure 29B:
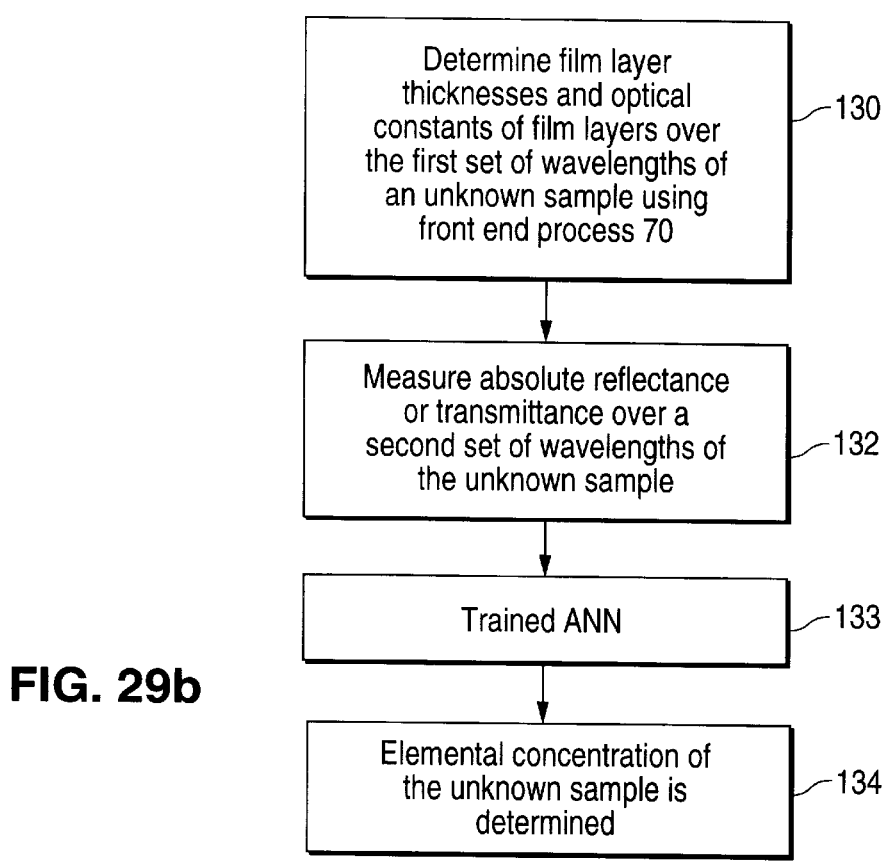

FIGS. 29*a* and 29*b* illustrates yet another embodiment of back end method 71 by which integrated optical measuring instrument 1 determines elemental concentration for sample substrate 38. This embodiment uses a trained ANN computer program to predict the concentration of one element from one film layer of a substrate overlaid with single or multiple films.

Figure 30:
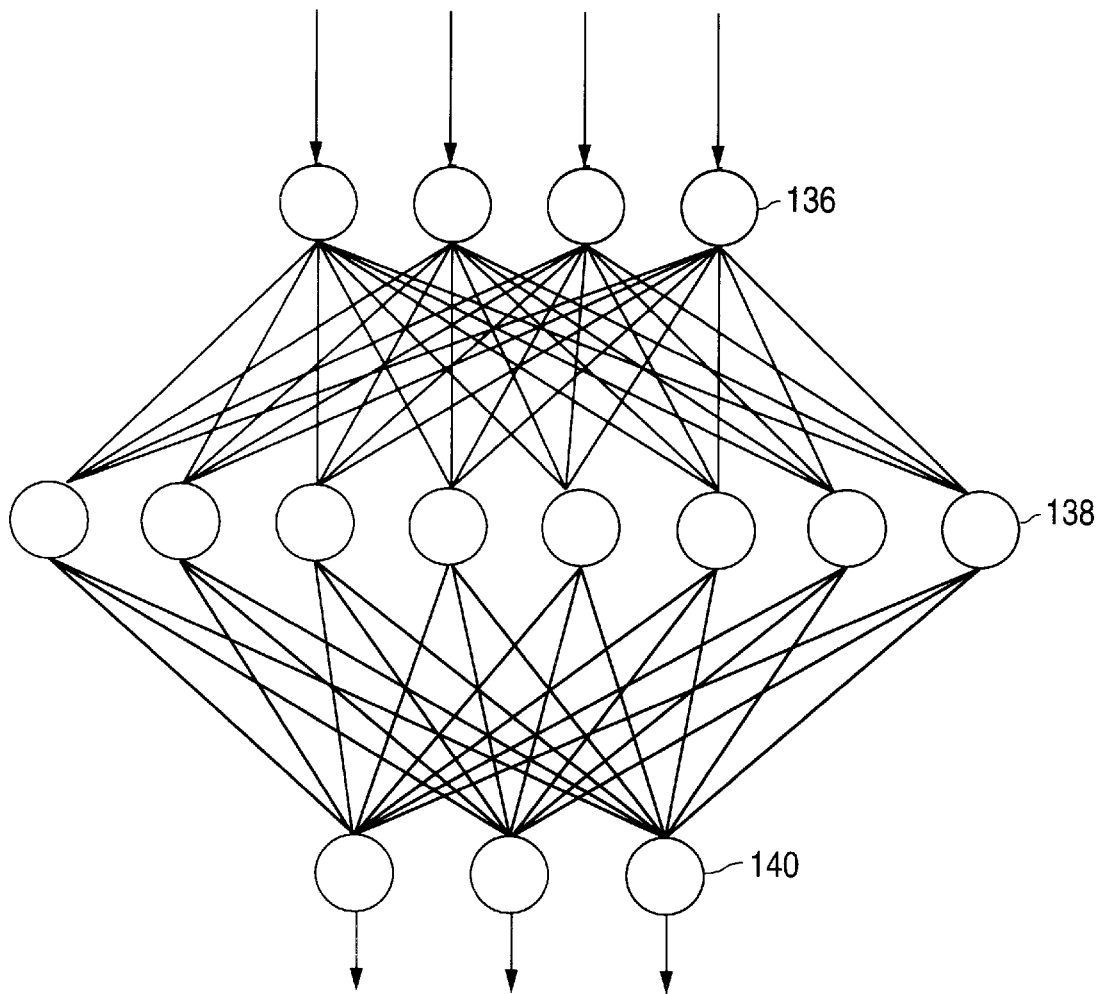
FIG. 30 is a schematic representation of an artificial neural network.

ANNs are computer programs that simulate the learning process of a human brain by using models of interconnected arrays of elementary processors known as neurons. There are a variety of different ANN architectures in use. FIG. 30 demonstrates a conventional ANN consisting of a certain number of input neurons 136, a certain number of output neuron 140, and zero or more intermediate layers of neurons 138 between the input and output neurons. Interconnections may be defined between any neurons, but they are usually limited to connections between neurons in adjacent layers. The connections between the neurons act as a link and pass a numeric value from one neuron to another. These values are weighted by a connection strength, which is adjusted during the training process to produce a final network. Each neuron, except for those in the input layer, receives a linearly weighted sum of all the outputs from the neurons of the previous layer. That neuron's value is then propagated through its connections to the neurons in the next layer. One example of commercially available ANN computer programs is "Qnet 97" made by Vesta Services Inc., located at 1001 Green Bay Road, Winnetka, Ill. 60093.

Thus, integrated optical measuring instrument 1, more specifically microprocessor 8 running an ANN computer program, e.g., Qnet 97, must first be trained with calibration samples with known elemental concentration. A supervised learning algorithm is employed to train the ANN computer program, where the ANN computer program is provided with a target output value for a given set of input parameters. FIG. 29a is a flow chart for calibrating the ANN computer program. In step 118, film layer thicknesses and optical constants of the film layers over a first set of wavelengths, e.g., VIS, are measured for a calibration sample using front end method 70 described above and in FIG. 5. In step 120, FTIR spectrometer 6 measures the calibration sample's absolute reflectance or transmittance over a second set of wavelengths, e.g., IR spectral range. In step 122, the user inputs the known concentration of the element. Steps 118, 120, and 122 are repeated for each calibration sample. In step 124, the ANN computer program is presented with the determined film layer thicknesses, the determined optical constants over the first set of wavelengths, the measured reflectance or transmittance over the second set of wavelengths of a calibration sample as input parameters, and the known concentration of the element in the calibration sample as the target value. The ANN computer program adjusts the interconnection weights to reduce the difference between predicted output and the target output value. In step 126, the user must decide if the training has provided results of a desired accuracy. The user can test the accuracy by inputting data from other calibration samples to compare the outputs to the known elemental concentrations. If the user is not satisfied by the results, step 124 is repeated with data from another calibration sample.

Once the ANN is trained, it is used to predict the concentration of that element when input with layer thicknesses, optical constants over the first set of wavelengths, e.g., VIS spectral range, and absolute reflectance or transmittance over the second set of wavelengths of an unknown specimen. FIG. 29b is a flow chart of the steps used to predict the concentration of the element. In step 130, film layer thicknesses and optical constants over the first set of wavelengths of sample substrate 38 are determined by front end method 70 described above and in FIG. 5. In step 132, FTIR spectrometer 6 measures absolute reflectance or transmittance over the second set of wavelengths. In step 133, the determined film layer thicknesses, the determined optical constants over the first set of wavelengths, and the measured absolute reflectance or transmittance over the second set of wavelengths are set as input values for the ANN. The values of the neurons of each successive layer are then calculated until a final value of the output neuron, i.e., the concentration of the element, is determined. Note that this process is very rapid because it is not iterative and only requires one set of calculations per layer of the ANN.

While the present disclosure discusses the use of a FTIR spectrometer in integrated optical measuring instrument 1 that measures absolute reflectance or transmittance over the second set of wavelengths, it should be understood that an embodiment of the present invention may also use spectral analysis instruments that measure reflectance, transmittance, ellipsometric parameters or any combination thereof, over the second set of wavelengths. Those of ordinary skill in the art will understand that additional measured spectral data helps the ANN computer program to more accurately predict elemental concentration.

Furthermore, while the present disclosure discusses the use of integrated optical measuring instrument 1, one skilled in the art will understand that the methods described above and in FIGS. 29a and 29b can be applied with separate optical measuring instruments. For example, a first optical measuring instrument can be used to determine film layer thicknesses and optical constants and a second optical measuring instrument can be used to measure IR reflectance, ellipsometric parameters, or transmittance. These values can then be input into an ANN computer program to determine elemental concentration.

Lastly, while the present disclosure discusses the determination of elemental concentration, it should be understood that the methods described above and throughout this disclosure are applicable for the measurement of the density of a chemical bond in the film. As previously discussed, one skilled in the art will understand that IR spectral measurements can be related to the type of a chemical bond between specific elements and the density of the chemical bond.

An embodiment comprising front end method 70 described above and in FIG. 5 and back end method 71 described above and in FIGS. 29a and 29b is demonstrated by the following example, where sixteen calibration samples of fluorinated silicon dioxide thin films are used to train the ANN to determine fluorine concentration. In this example, the sixteen calibration samples used in the previous example for back end method 71 described above and in FIGS. 18a and 18b are used again. The ANN is first trained with fourteen of the sixteen calibration samples. The ANN is then tested for accuracy with the two remaining calibration samples.

Figure 31:
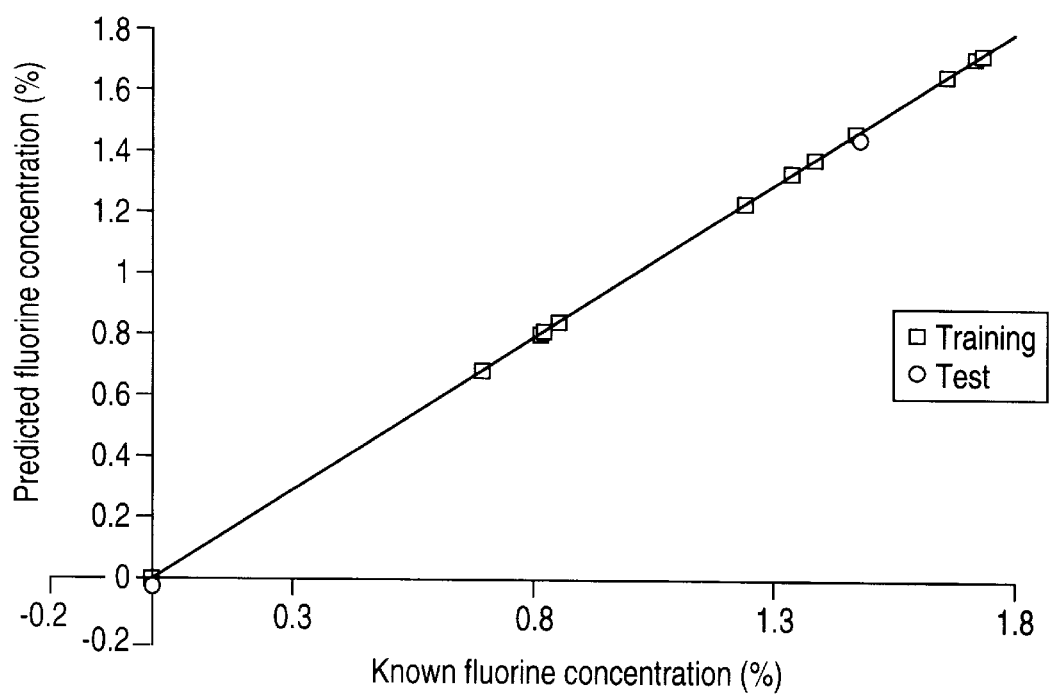
FIG. 31 is a graph of the fluorine concentration predicated by a trained artificial neural network computer program against the known fluorine concentration.

Following the flow chart of FIG. 29a, the film layer thicknesses and optical constants over the first set of wavelengths of each calibration sample are determined by front end method 70 described above and in FIG. 5. Next, the absolute reflectance over the second set of wavelengths of each calibration sample is measured. The determined film layer thicknesses, the determined optical constants over the first set of wavelengths, and the measured absolute reflectance over the second set of wavelengths for each calibration sample are presented to the ANN as input values, while the corresponding known fluorine concentration of each calibration sample is presented to the ANN as the target output value. As FIG. 31 demonstrates, the ANN produces a good correspondence between the known and the predicted fluorine concentrations of the twelve training calibration samples. More importantly, when presented with data for the two remaining test calibration samples, FIG. 31 demonstrates that the ANN provides a good correspondence between the known and the predicted fluorine concentrations.

Although the present invention has been described in considerable detail to specific embodiments, numerous variations and modifications are possible. Therefore, the scope of the appended claims is not limited to the description of the specific embodiments described herein.

What is claimed is:

1. A method comprising:
    measuring reflectances, ellipsometric parameters, or transmittances of a first area of a film layer structure on a substrate over a first set of wavelengths while the substrate is in a first position, wherein the film layer structure includes a selected film layer;
    measuring reflectances, ellipsometric parameters, or transmittances of a second area of the film layer structure on the substrate over a second set of wavelengths while the substrate is in the first position;
    determining a thickness of the selected film layer; and
    determining a concentration of an element or a density of a chemical bond in the selected film layer based on the determined thickness.

2. The method of claim 1, wherein determining the thickness of the selected film layer comprises:

providing an optical model of the film layer structure on the substrate;

calculating theoretical reflectances, theoretical ellipsometric parameters, or theoretical transmittances over the first set of wavelengths with a first set of parameters, wherein the first set of parameters includes the thickness and optical constants of the selected film layer over the first set of wavelengths; and adjusting the first set of parameters to calculate theoretical reflectances, theoretical ellipsometric parameters, or theoretical transmittances over the first set of wavelengths to approximate the measured reflectances, the measured ellipsometric parameters, or the measured transmittances over the first set of wavelengths.

3. The method of claim 2, wherein adjusting the first set of parameters comprises using a Levenberg-Marquardt nonlinear multivariate regression algorithm to adjust the first set of parameters in the optical model.

4. The method of claim 2, further comprising representing the optical constants over the first set of wavelengths of the selected film layer in the optical model by a parametric dispersion model.

5. The method of claim 2, wherein determining the concentration of the element or the density of the chemical bond in the selected film layer comprises:

calculating theoretical reflectances, theoretical ellipsometric parameters, or theoretical transmittances with the optical model over the second set of wavelengths from the determined thickness of the selected film layer and a second set of parameters, wherein the second set of parameters includes optical constants of the selected film layer over the second set of wavelengths;

adjusting the second set of parameters to calculate theoretical reflectances, theoretical ellipsometric parameters, or theoretical transmittances over the second set of wavelengths to approximate the measured reflectances, the measured ellipsometric parameters, or the measured transmittances over the second set of wavelengths;

selecting optical constants of the selected film layer at a wavelength of an absorption band of the element or the chemical bond; and relating the optical constants of the selected film layer at the wavelength of the absorption band to the concentration of the element or the density of the chemical bond.

6. The method of claim 5, wherein adjusting the second set of parameters comprises using the Levenberg-Marquardt nonlinear multivariate regression algorithm to adjust the second set of parameters in the optical model.

7. The method of claim 5, further comprising representing the optical constants over the second set of wavelengths of the selected film layer in the optical model by a parametric dispersion model.

8. The method of claim 7, further comprising determining the concentration of the element or the density of the chemical bond in the selected film layer from the parametric dispersion model representing the optical constants over the second set of wavelengths of the selected film layer.

9. A method comprising:

determining a thickness of a selected film layer in a film layer structure on a substrate;

determining an absorption-related feature of an element or a chemical bond, wherein the absorption-related feature is an area of a peak or valley of an absorption band of the element or the chemical bond; and determining a concentration of the element or a density of the chemical bond in the selected film layer based on the determined thickness and the determined absorption-related feature.

10. The method of claim 9, wherein determining the thickness of the selected film layer comprises:

measuring reflectances, ellipsometric parameters, or transmittances of a first area of the film layer structure on the substrate over a first set of wavelengths;

providing an optical model of the film layer structure on the substrate;

calculating theoretical reflectances, theoretical ellipsometric parameters, or theoretical transmittances over the first set of wavelengths with a set of parameters, wherein the set of parameters includes the thickness and optical constants of the selected film layer over the first set of wavelengths; and adjusting the set of parameters to calculate theoretical reflectances, theoretical ellipsometric parameters, or theoretical transmittances over the first set of wavelengths to approximate the measured reflectances, the measured ellipsometric parameters, or the measured transmittances over the first set of wavelengths.

11. The method of claim 10, wherein adjusting the set of parameters comprises using a Levenberg-Marquardt nonlinear multivariate regression algorithm to adjust the parameters in the optical model.

12. The method of claim 10, further comprising representing the optical constants over the first set of wavelengths of the selected film layer in the optical model by a parametric dispersion model.

13. The method of claim 9, wherein determining the absorption-related feature of the element or the chemical bond comprises:

measuring reflectances or transmittances of a second area of the film layer structure on the substrate over a second set of wavelengths; and determining the absorption-related feature from the measured reflectances or the measured transmittances over the second set of wavelengths.

14. The method of claim 13, wherein determining the concentration of the element or the density of the chemical bond in the selected film layer comprises:

relating the determined thickness of the selected film layer and the determined absorption-related feature to the concentration of the element or the density of the chemical bond by:

$$C(t, A_p) = \sum_{i=1}^{N} c_i \cdot f_i(t, A_p),$$

where C is the concentration of the element or the density of the chemical bond, $c_i$ represents constants for the element or the chemical bond, N is the total number of the constants $c_i$ and the minimum number of calibration films necessary to solve the constants $c_i$, t is the thickness of the selected film layer, $A_p$ is the absorption-related feature, and $f_i(t, A_p)$ is a function of t and $A_p$.

15. The method of claim 14, wherein the constants $c_i$ are determined from calibration films with known concentrations of the element or known densities of the chemical bond by:

determining film layer thicknesses for each of the calibration films;

measuring reflectances or transmittances over the second set of wavelengths for each of the calibration films;

determining the absorption-related feature from the reflectances or transmittances over the second set of wavelengths for each of the calibration films; and solving for the constants $c_i$ with the known concentrations of the element or the known densities of the chemical bond, the measured film layer thicknesses, and the determined absorption-related feature values of the calibration films.

16. The method of claim 14, wherein $C(t,A_p)$ is further defined as:

$$C(t,A_p)=(c_1+c_2t+c_3t^2)+(c_4+c_5t+c_6t^2)A_p+(c_7+c_8t+c_9t^2)A_p^2,$$

where $c_1$ through $c_9$ are constants for the element or the chemical bond.

17. A method comprising:

determining a thickness and optical constants of a selected film layer in a film layer structure on a substrate, wherein the optical constants are determined over a first set of wavelength;

measuring reflectances, ellipsometric parameters, or transmittances of the film layer structure on the substrate over a second set of wavelengths;

inputting into an artificial neural network the determined thickness of the selected film layer, the determined optical constants of the selected film layer, the measured reflectances over the second set of wavelengths, the measured ellipsometric parameters over the second set of wavelengths, or the measured transmittances over the second set of wavelengths; and determining a concentration of an element or a density of a chemical bond in the selected film layer of the film layer structure on the substrate.

18. The method of claim 17, further comprising training the artificial neural network with calibration films having known concentrations of the element or known densities of the chemical bond by:

measuring reflectances, ellipsometric parameters, or transmittances over the first set of wavelengths for each of the calibration films;

determining film layer thicknesses and optical constants over the first set of wavelengths for each of the calibration films;

measuring reflectances, ellipsometric parameters, or transmittances over the second set of wavelengths for each of the calibration films;

inputting into the artificial neural network the determined film layer thicknesses, the determined optical constants of the film layers over the first set of wavelengths, the measured reflectances over the second set of wavelengths, the measured ellipsometric parameters over the second set of wavelengths, or the measured transmittances over the second set of wavelengths of the calibration films; and inputting into the artificial neural network the known concentrations of the element or the known densities of the chemical bond of the calibration films as target outputs, wherein the artificial neural network is adjusted to calculate the target outputs.

19. The method of claim 17, wherein determining the thickness and the optical constants of the selected film layer comprises:

measuring reflectances, ellipsometric parameters, or transmittances of the film layer structure on the substrate over the first set of wavelengths;

providing an optical model of the film layer structure on the substrate;

calculating theoretical reflectances, theoretical ellipsometric parameters, or theoretical transmittances over the first set of wavelengths with a set of parameters, wherein the set of parameters includes the thickness and the optical constants of the selected film layer; and adjusting the set of parameters to calculate theoretical reflectances, theoretical ellipsometric parameters, or theoretical transmittances over the first set of wavelengths to approximate the measured reflectances, the measured ellipsometric parameters, or the measured transmittances over the first set of wavelengths.

20. The method of claim 19, wherein adjusting the set of parameters comprises using a Levenberg-Marquardt nonlinear multivariate regression algorithm to adjust the parameters in the optical model.

21. The method of claim 19, further comprising representing the optical constants of the selected film layer in the optical model by a parametric dispersion model.

* * * * *

UNITED STATES PATENT AND TRADEMARK OFFICE
CERTIFICATE OF CORRECTION

PATENT NO. : 6,381,009 B1
DATED : April 30, 2002
INVENTOR(S) : Jean Pierre Burtin and Caryl Thome It is certified that error appears in the above-identified patent and that said Letters Patent is hereby corrected as shown below:

<u>Column 4,</u>
Line 7, delete "14and" and insert therefor -- 14 and --

<u>Column 6,</u>
Line 3, delete "13" and insert therefore -- 13 --
Line 24, delete "$I^{max}$" and insert therefore -- $I_{max}$ --

Signed and Sealed this

Fifth Day of November, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,381,009 B1 Page 1 of 1
DATED : April 30, 2002
INVENTOR(S) : William A. McGahan It is certified that error appears in the above-identified patent and that said Letters Patent is hereby corrected as shown below:

This certificate supersedes Certificate of Correction issued November 5, 2002, the number was erroneously mentioned and should be vacated since no Certificate of Correction was granted.

Signed and Sealed this

Fourth Day of February, 2003

JAMES E. ROGAN
*Director of the United States Patent and Trademark Office*

UNITED STATES PATENT AND TRADEMARK OFFICE
CERTIFICATE OF CORRECTION

PATENT NO.      : 6,381,009 B1
DATED           : April 30, 2002
INVENTOR(S)     : William A. McGahan It is certified that error appears in the above-identified patent and that said Letters Patent is hereby corrected as shown below:

Column 13,
Line 27, "M-7161 US" should be -- layer thickness and the absorption related feature --.

Signed and Sealed this

Fourth Day of January, 2005

JON W. DUDAS
*Director of the United States Patent and Trademark Office*